US012465390B2

(12) United States Patent
Gee et al.

(10) Patent No.: US 12,465,390 B2
(45) Date of Patent: Nov. 11, 2025

(54) ELECTRODES AND METHODS FOR USE WITH A MULTI-LAYER CLAMP ARM PAD TO ENHANCE THE PERFORMANCE OF A SURGICAL DEVICE

(71) Applicant: Cilag GmbH International, Zug (CH)

(72) Inventors: Jacob S. Gee, Cincinnati, OH (US); Michael A. Keenan, Cincinnati, OH (US); William A. Olson, Lebanon, OH (US); Tyler N. Brehm, Cincinnati, OH (US); Cameron D. McLain, Fairfield, OH (US); Kevin Price, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 343 days.

(21) Appl. No.: 17/963,725

(22) Filed: Oct. 11, 2022

(65) Prior Publication Data

US 2023/0128575 A1 Apr. 27, 2023

Related U.S. Application Data

(60) Provisional application No. 63/271,410, filed on Oct. 25, 2021.

(51) Int. Cl.
*A61B 17/32* (2006.01)
*A61B 17/00* (2006.01)

(52) U.S. Cl.
CPC ................. *A61B 17/320092* (2013.01); *A61B 2017/00026* (2013.01); *A61B 2017/320073* (2017.08)

(58) Field of Classification Search
CPC .. A61B 17/320092; A61B 2017/30073; A61B 2017/00026; A61B 2017/32095; A61B 18/1445; A61B 18/00994
See application file for complete search history.

(56) References Cited

U.S. PATENT DOCUMENTS

| | | | | |
|---|---|---|---|---|
| 8,623,018 | B2 * | 1/2014 | Horner .............. | A61B 18/1442 606/51 |
| 8,745,840 | B2 | 6/2014 | Hempstead et al. | |
| 9,901,359 | B2 | 2/2018 | Faller et al. | |

(Continued)

OTHER PUBLICATIONS

IEEE Std 802.Mar. 2012 (Revision of IEEE Std 802.Mar. 2008, published Dec. 28, 2012.

(Continued)

*Primary Examiner* — Tan-Uyen T Ho
*Assistant Examiner* — Cherie M Poland

(57) ABSTRACT

A surgical device, is disclosed herein. The surgical device can include an end effector including a clamp jaw, a trigger configured to open and close the clamp jaw, a sensor configured to detect a relative position of the trigger, and a control circuit communicably coupled to the sensor and a generator, wherein the control circuit is configured to cause the generator to administer energy associated with a surgical operation to be performed on the tissue, receive a signal from the sensor, determine that the clamp jaws are not positioned to administer the energy associated with the surgical operation, and cause the generator to administer energy configured to release the tissue from an ultrasonic blade, wherein the energy configured to release the tissue from the clamp jaw is different than the energy associated with a surgical operation to be performed on the tissue.

9 Claims, 20 Drawing Sheets

(56) References Cited

U.S. PATENT DOCUMENTS 10,231,777 B2 3/2019 Brandt et al.
10,624,691 B2 4/2020 Wiener et al.
11,013,528 B2 5/2021 Isosaki et al.
11,259,830 B2 3/2022 Nott et al.
11,266,430 B2 3/2022 Clauda et al.
11,317,937 B2 5/2022 Nott et al.
11,464,532 B2 10/2022 Nott et al.
11,589,916 B2 2/2023 Shelton, IV et al.
11,684,412 B2 6/2023 Shelton, IV et al.
11,696,776 B2 7/2023 Shelton, IV et al.
11,707,318 B2 7/2023 Shelton, IV et al.
11,723,716 B2 8/2023 Fiebig et al.
11,744,636 B2 9/2023 Shelton, IV et al.
11,759,251 B2 9/2023 Shelton, IV et al.
11,779,387 B2 10/2023 Salguero et al.
11,786,291 B2 * 10/2023 Sarley .................... A61B 90/03 606/45
11,786,294 B2 10/2023 Shelton, IV et al.
11,944,366 B2 * 4/2024 Faller ................. A61B 18/1442
11,994,366 B2 * 5/2024 Sitrick ...................... F41G 3/02
2003/0114874 A1 6/2003 Craig et al.
2006/0030848 A1 2/2006 Craig et al.
2013/0267975 A1 * 10/2013 Timm ............ A61B 17/320068 606/169
2017/0105754 A1 * 4/2017 Boudreaux ........ A61B 18/1445
2017/0105755 A1 * 4/2017 Boudreaux ........ A61B 18/1445
2017/0105788 A1 * 4/2017 Boudreaux .... A61B 17/320092
2018/0132887 A1 * 5/2018 Asher ................ A61B 18/1445
2018/0271575 A1 * 9/2018 Dix .................... A61B 17/7098
2018/0271578 A1 * 9/2018 Coulombe ............. A61B 18/02
2019/0069949 A1 * 3/2019 Vrba ...................... A61B 18/02
2019/0201042 A1 7/2019 Nott et al.
2019/0274720 A1 * 9/2019 Gee ................ A61B 17/320068
2020/0352636 A1 11/2020 Batchelor et al.
2021/0196305 A1 7/2021 Strobl
2021/0196306 A1 7/2021 Estera et al.
2021/0196307 A1 7/2021 Shelton, IV
2021/0196334 A1 7/2021 Sarley et al.
2021/0196335 A1 7/2021 Messerly et al.
2021/0196336 A1 7/2021 Faller et al.
2021/0196344 A1 7/2021 Shelton, IV et al.
2021/0196345 A1 7/2021 Messerly et al.
2021/0196346 A1 7/2021 Leuck et al.
2021/0196349 A1 7/2021 Fiebig et al.
2021/0196352 A1 7/2021 Messerly et al.
2021/0196353 A1 * 7/2021 Gee ................ A61B 17/320092
2021/0196354 A1 7/2021 Shelton, IV et al.
2021/0196357 A1 7/2021 Shelton, IV et al.
2021/0196358 A1 7/2021 Shelton, IV et al.
2021/0196359 A1 7/2021 Shelton, IV et al.
2021/0196361 A1 7/2021 Shelton, IV et al.
2021/0196362 A1 7/2021 Shelton, IV et al.
2021/0196363 A1 7/2021 Shelton, IV et al.
2021/0196364 A1 7/2021 Shelton, IV et al.

OTHER PUBLICATIONS

"ATM-MPLS Network Interworking Version 2.0, af-aic-0178.001" ATM Standard, The ATM Forum Technical Committee, published Aug. 2003.

* cited by examiner

3120

3130

3140

3150

ELECTRODES AND METHODS FOR USE WITH A MULTI-LAYER CLAMP ARM PAD TO ENHANCE THE PERFORMANCE OF A SURGICAL DEVICE

CROSS-REFERENCE TO RELATED APPLICATIONS

This application claims the benefit of priority under 35 U.S.C. § 119(e) to U.S. Provisional Patent Application No. 63/271,410, titled ELECTRODES AND METHODS FOR USE WITH A MULTI-LAYER CLAMP ARM PAD TO ENHANCE THE PERFORMANCE OF A SURGICAL DEVICE, filed on Oct. 25, 2021, the disclosure of which is herein incorporated by reference in its entirety.

TECHNICAL FIELD

The present disclosure generally relates to end-effectors adapted and configured to operate with multiple energy modalities to enable tissue sealing and cutting employing simultaneously, independently, or sequentially applied energy modalities. More particularly, the present disclosure relates to end-effectors adapted and configured to operate with surgical instruments that employ combined ultrasonic and electrosurgical systems, such as monopolar or bipolar radio frequency (RF), to enable tissue sealing and cutting employing simultaneously, independently, or sequentially applied ultrasonic and electrosurgical energy modalities. The energy modalities may be applied based on tissue parameters or other algorithms. The end-effectors may be adapted and configured to couple to hand held or robotic surgical systems.

BACKGROUND

Ultrasonic surgical instruments employing ultrasonic energy modalities are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an end-effector, ultrasonic blade, or ultrasonic blade tip, at the distal end of the instrument, which transmits ultrasonic energy to tissue brought into contact with the end-effector. An ultrasonic end-effector may comprise an ultrasonic blade, a clamp arm, and a pad, among other components.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical instruments for applying electrical energy modalities to tissue to treat, seal, cut, and/or destroy tissue also are finding increasingly widespread applications in surgical procedures. An electrosurgical instrument typically includes an instrument having a distally-mounted end-effector comprising one or more than one electrode. The end-effector can be positioned against the tissue such that electrical current is introduced into the tissue. Electrosurgical instruments can be configured for bipolar or monopolar operation. During bipolar operation, current is introduced though a first electrode (e.g., active electrode) into the tissue and returned from the tissue through a second electrode (e.g., return electrode). During monopolar operation, current is introduced into the tissue by an active electrode of the end-effector and returned through a return electrode such as a grounding pad, for example, separately coupled to the body of a patient. Heat generated by the current flowing through the tissue may form hemostatic seals within the tissue and/or between tissues and thus may be particularly useful for sealing blood vessels, for example. The end-effector of an electrosurgical instrument also may include a cutting member that is movable relative to the tissue and the electrodes to transect the tissue. Electrosurgical end-effectors may be adapted and configured to couple to hand held instruments as well as robotic instruments.

Electrical energy applied by an electrosurgical instrument can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601 2:2009+A11:2011, Definition 201.3.218—HIGH FREQUENCY. For example, the frequency in monopolar RF applications may be typically restricted to less than 5 MHz. However, in bipolar RF energy applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Ultrasonic surgical instruments and electrosurgical instruments of the nature described herein can be configured for open surgical procedures, minimally invasive surgical procedures, or non-invasive surgical procedures. Minimally invasive surgical procedures involve the use of a camera and instruments inserted through small incisions in order to visualize and treat conditions within joints or body cavities. Minimally invasive procedures may be performed entirely within the body or, in some circumstances, can be used together with a smaller open approach. These combined approaches, known as "arthroscopic, laparoscopic or thoracoscopic-assisted surgery," for example. The surgical instruments described herein also can be used in non-invasive procedures such as endoscopic surgical procedures, for example. The instruments may be controlled by a surgeon using a hand held instrument or a robot.

A challenge of utilizing these surgical instruments is the inability to control and customize single or multiple energy modalities depending on the type of tissue being treated. It would be desirable to provide end-effectors that overcome some of the deficiencies of current surgical instruments and improve the quality of tissue treatment, sealing, or cutting or combinations thereof. The combination energy modality end-effectors described herein overcome those deficiencies and improve the quality of tissue treatment, sealing, or cutting or combinations thereof.

SUMMARY

In one aspect, an apparatus is provided for dissecting and coagulating tissue. The apparatus comprises a surgical instrument comprising an end-effector adapted and configured to deliver a plurality of energy modalities to tissue at a distal end thereof. The energy modalities may be applied simultaneously, independently, or sequentially. A generator is electrically coupled to the surgical instrument and is configured to supply a plurality of energy modalities to the end-effector. In one aspect, the generator is configured to supply electrosurgical energy (e.g., monopolar or bipolar radio frequency (RF) energy) and ultrasonic energy to the end-effector to allow the end-effector to interact with the tissue. The energy modalities may be supplied to the end-effector by a single generator or multiple generators.

In various aspects, the present disclosure provides a surgical instrument configured to deliver at least two energy types (e.g., ultrasonic, monopolar RF, bipolar RF, microwave, or irreversible electroporation [IRE]) to tissue. The surgical instrument includes a first activation button for activating energy, a second button for selecting an energy mode for the activation button. The second button is connected to a circuit that uses at least one input parameter to define the energy mode. The input parameter can be modified remotely through connection to a generator or through a software update.

In one aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the at least one electrode acts a deflectable support with respect to an opposing ultrasonic blade. The at least one electrode crosses over the ultrasonic blade and is configured to be deflectable with respect to the clamp arm having features to change the mechanical properties of the tissue compression under the at least one electrode. The at least one electrode includes a feature to prevent inadvertent contact between the electrode and the ultrasonic blade.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the movable clamp jaw comprises at least one non-biased deflectable electrode to minimize contact between the ultrasonic blade and the RF electrode. The ultrasonic blade pad contains a feature for securing the electrode to the pad. As the pad height wears or is cut through, the height of the electrode with respect to the clamp jaw is progressively adjusted. Once the clamp jaw is moved away from the ultrasonic blade, the electrode remains in its new position.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the at least one bipolar RF electrode is deflectable and has a higher distal bias than proximal bias. The bipolar RF electrode is deflectable with respect to the clamp jaw. The end-effector is configured to change the mechanical properties of the tissue compression proximal to distal end to create a more uniform or differing pattern of pressure than due to the clamping alone.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the bipolar RF electrode is deflectable and the end-effector provides variable compression/bias along the length of the deflectable electrode. The end-effector is configured to change the mechanical properties of the tissue compression under the electrodes based on clamp jaw closure or clamping amount.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. The one aspect, the pad includes asymmetric segments to provide support for the ultrasonic blade support and the electrode is movable. The asymmetric segmented pad is configured for cooperative engagement with the movable bipolar RF electrode. The segmented ultrasonic support pad extends at least partially through the bipolar RF electrode. At least one pad element is significantly taller than a second pad element. The first pad element extends entirely through the bipolar RF electrode and the second pad element extends partially through the bipolar RF electrode. The first pad element and the second pad element are made of dissimilar materials.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, variations in the physical parameters of the electrode in combination with a deflectable electrode are employed to change the energy density delivered to the tissue and the tissue interactions. The physical aspects of the electrode vary along its length in order to change the contact area and/or the energy density of the electrode to tissue as the electrode also deflects.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, an ultrasonic transducer control algorithm is provided to reduce the power delivered by the ultrasonic or RF generator when a short circuit of contact between the ultrasonic blade and the electrode is detected to prevent damage to the ultrasonic blade. The ultrasonic blade control algorithm monitors for electrical shorting or ultrasonic blade to electrode contact. This detection is used to adjust the power/amplitude level of the ultrasonic transducer when the electrical threshold minimum is exceeded and adjusts the transducer power/amplitude threshold to a level below the minimum threshold that would cause damage to the ultrasonic blade, ultrasonic generator, bipolar RF electrode, or bipolar RF generator. The monitored electrical parameter could be tissue impedance (Z) or electrical continuity. The power adjustment could be to shut off the ultrasonic generator, bipolar RF generator, of the surgical device or it could be a proportionate response to either the electrical parameter, pressure, or time or any combination of these parameters.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the clamp jaw features or aspects are provided in the clamp ram to minimize tissue sticking and improve tissue control. The clamp arm tissue path or clamp area includes features configured to adjust the tissue path relative to the clamp arm/ultrasonic blade to create a predefined location of contact to reduce tissue sticking and charring.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, a partially conductive clamp arm pad is provided to enable electrode wear through and minimize electrical shorting between the ultrasonic blade and the bipolar RF electrode. The clamp arm pad includes electrically conductive and non-conductive portions allowing it to act as one of the bipolar RF electrodes while also acting as the wearable support structure for the ultrasonic blade. The electrically conductive portions of the clamp ram pad are positioned around the perimeter of the pad and not positioned directly below the ultrasonic blade contact area. The electrically conductive portion is configured to degrade or wear to prevent any contact with the ultrasonic blade from interrupting the electrical conductivity of the remaining electrically conductive pad.

In another aspect, the present disclosure provides an end-effector configured to grasp tissue. The end-effector includes an ultrasonic blade configured to be coupled to an ultrasonic transducer and a clamp arm, including a clamp arm pad. The ultrasonic blade is configured to transfer ultrasonic energy to the tissue. The clamp arm pad includes an electrically conductive material, and an electrically non-conductive material. The clamp arm pad is configured as an electrode of a radiofrequency energy circuit. The electrode is configured to transfer radiofrequency energy through the tissue to a return electrode of the radiofrequency energy circuit. The electrically non-conductive material is configured to reduce the possibility of an electrical short between the electrically conductive material and the ultrasonic blade as the clamp arm pad degrades throughout the usable life of the end effector.

In another aspect, the present disclosure provides a clamp arm configured to grasp tissue in conjunction with an ultrasonic blade. The clamp arm includes a clamp arm pad including an electrically conductive layer defining a channel and an electrically non-conductive layer. The electrically non-conductive layer is positioned adjacent the electrically conductive layer such that at least a portion of the electrically non-conductive layer is positioned through the channel. The clamp arm pad is configured as an electrode of a radiofrequency energy circuit. The electrically non-conductive material is configured to reduce the possibility of an electrical short between the electrically conductive material and the ultrasonic blade.

In another aspect, the present disclosure provides an end-effector configured to grasp tissue. The end-effector includes an ultrasonic blade and a clamp arm including a clamp arm pad. The clamp arm pad includes an electrically conductive material and an electrically non-conductive material. The electrically non-conductive material is configured to prevent the electrically conductive material from being positioned a predetermined distance away from the ultrasonic blade as the clamp arm pad degrades throughout the usable life of the end effector.

In another aspect, the present disclosure provides a surgical device. The surgical device can include an end effector including a clamp jaw, a trigger configured to open and close the clamp jaw, a sensor configured to detect a relative position of the trigger, and a control circuit communicably coupled to the sensor and a generator, wherein the control circuit is configured to cause the generator to administer energy associated with a surgical operation to be performed on the tissue, receive a signal from the sensor, determine that a user is trying to release the tissue from the clamp jaws based on the signal, and cause the generator to administer energy configured to release the tissue from the clamp jaw in response to determining that the user is trying to release the tissue from the clamp jaws, wherein the energy configured to release the tissue from the clamp jaw is different than the energy associated with a surgical operation to be performed on the tissue.

In another aspect, the present disclosure provides an end effector configured for use with a surgical device. The end effector can include a clamp arm base, a clamp arm pad including a first geometry, an ultrasonic blade including a first hardness; and an electrode. The electrode can include an electrode material including a second hardness, wherein the second hardness is less than the first hardness of the ultrasonic blade, and wherein the electrode material defines a cavity including a second geometry. The second geometry can correspond to the first geometry such that a portion of the clamp arm pad can be positioned within the cavity; and an intermediate material configured to adhere the electrode material to the clamp arm base.

In another aspect, the present disclosure provides a method of manufacturing an electrode configured for use within an end effector of a surgical device. The method can include forming an electrode material into a desired geometrical configuration, forming one or more pockets into the electrode material, and applying an intermediate material into the one or more pockets formed into the electrode, wherein the intermediate material is suited for welding, bonding the intermediate material to the electrode material. The method can further include attaching the intermediate material to a clamp arm base of the end effector to secure the intermediate material and electrode material to the clamp arm base.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

DESCRIPTION

Figure 1:
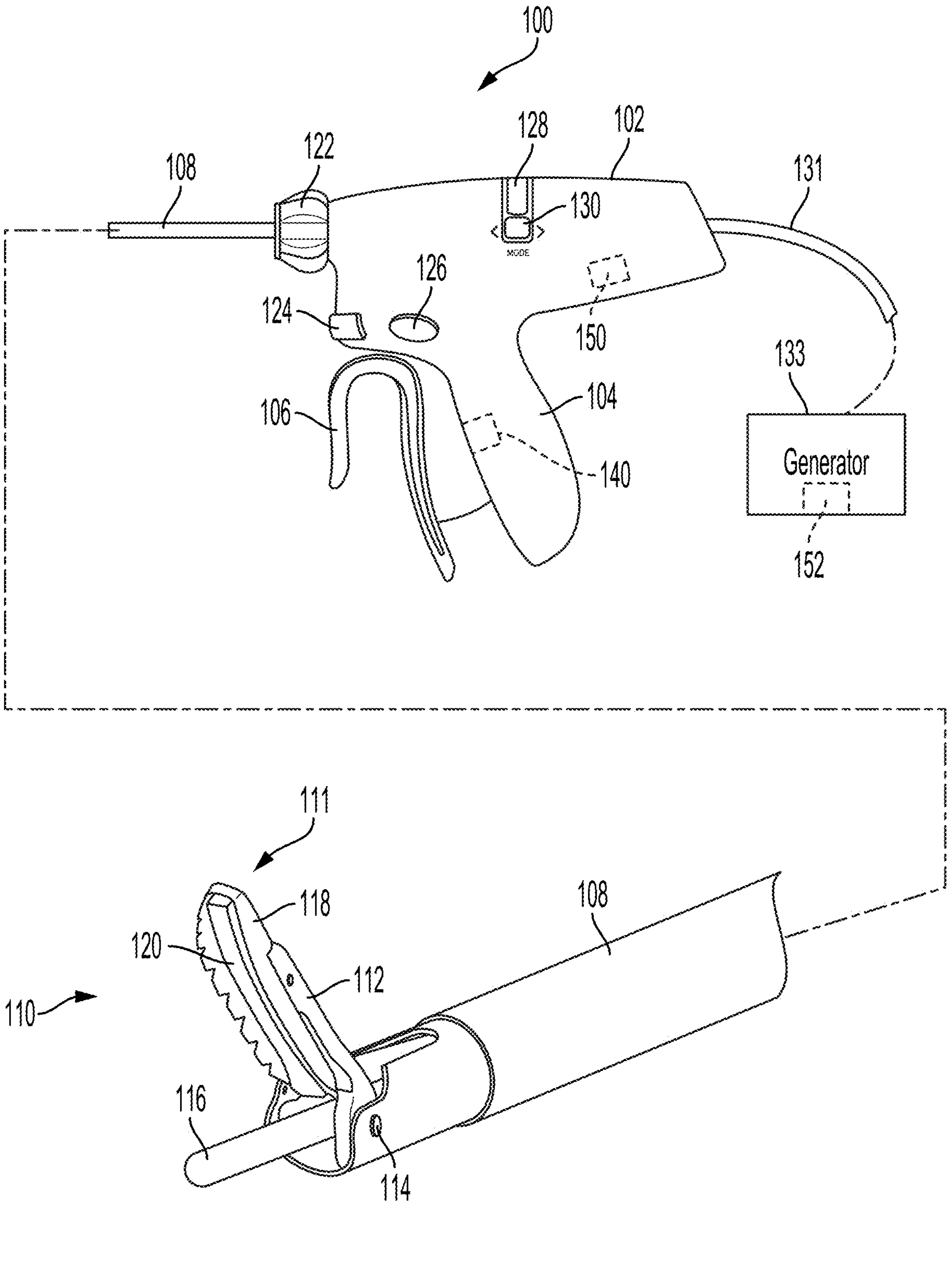
FIG. 1 illustrates a surgical device, according to at least one aspect of the present disclosure.

Applicant of the present application owns the following U.S. Provisional Patent Applications, filed on Dec. 30, 2019, the disclosure of each of which is hereby incorporated by reference in its respective entirety: U.S. Provisional Patent Application Ser. No. 62/955,294, entitled USER INTERFACE FOR SURGICAL INSTRUMENT WITH COMBINATION ENERGY MODALITY END-EFFECTOR; U.S. Provisional Patent Application Ser. No. 62/955,299, entitled ELECTROSURGICAL INSTRUMENTS FOR COMBINATION ENERGY DELIVERY; and U.S. Provisional Patent Application Ser. No. 62/955,306, entitled SURGICAL INSTRUMENTS.

Applicant of the present application owns the following U.S. Patent Applications filed on May 28, 2020, each of which is hereby incorporated by reference in its respective entirety: U.S. patent application Ser. No. 16/887,499, entitled USER INTERFACE FOR SURGICAL INSTRUMENT WITH COMBINATION ENERGY MODALITY END-EFFECTOR; U.S. patent application Ser. No. 16/887,493, entitled METHOD OF OPERATING A COMBINATION ULTRASONIC/BIPOLAR RF SURGICAL DEVICE WITH A COMBINATION ENERGY MODALITY END-EFFECTOR; U.S. patent application Ser. No. 16/887,506, entitled DEFLECTABLE SUPPORT OF RF ENERGY ELECTRODE WITH RESPECT TO OPPOSING ULTRASONIC BLADE; U.S. patent application Ser. No. 16/887,515, entitled NON-BIASED DEFLECTABLE ELECTRODE TO MINIMIZE CONTACT BETWEEN ULTRASONIC BLADE AND ELECTRODE; U.S. patent application Ser. No. 16/887,519, entitled DEFLECTABLE ELECTRODE WITH HIGHER DISTAL BIAS RELATIVE TO PROXIMAL BIAS; U.S. patent application Ser. No. 16/887,532, entitled DEFLECTABLE ELECTRODE WITH VARIABLE COMPRESSION BIAS ALONG THE LENGTH OF THE DEFLECTABLE ELECTRODE; U.S. patent application Ser. No. 16/887,554, entitled ASYMMETRIC SEGMENTED ULTRASONIC SUPPORT PAD FOR COOPERATIVE ENGAGEMENT WITH A MOVABLE RF ELECTRODE; U.S. patent application Ser. No. 16/887,561, entitled VARIATION IN ELECTRODE PARAMETERS AND DEFLECTABLE ELECTRODE TO MODIFY ENERGY DENSITY AND TISSUE INTERACTION; U.S. patent application Ser. No. 16/887,568, entitled TECHNIQUES FOR DETECTING ULTRASONIC BLADE TO ELECTRODE CONTACT AND REDUCING POWER TO ULTRASONIC BLADE; U.S. patent application Ser. No. 16/887,576, entitled CLAMP ARM JAW TO MINIMIZE TISSUE STICKING AND IMPROVE TISSUE CONTROL; U.S. patent application Ser. No. 16/887,579, entitled PARTIALLY CONDUCTIVE CLAMP ARM PAD TO ENABLE ELECTRODE WEAR THROUGH AND MINIMIZE SHORT CIRCUITING; U.S. patent application Ser. No. 10/289,787, entitled ULTRASONIC CLAMP COAGULATOR APPARATUS HAVING AN IMPROVED CLAMPING END-EFFECTOR; and U.S. patent application Ser. No. 11/243,585, entitled ULTRASONIC CLAMP COAGULATOR APPARATUS HAVING AN IMPROVED CLAMPING END-EFFECTOR.

Applicant of the present application owns the following U.S. Patent Applications filed on May 28, 2020, each of which is hereby incorporated by reference in its respective entirety: U.S. patent application Ser. No. 16/885,813, entitled METHOD FOR AN ELECTROSURGICAL PROCEDURE; U.S. patent application Ser. No. 16/885,820, entitled ARTICULATABLE SURGICAL INSTRUMENT; U.S. patent application Ser. No. 16/885,823, entitled SURGICAL INSTRUMENT WITH JAW ALIGNMENT FEATURES; U.S. patent application Ser. No. 16/885,826, entitled SURGICAL INSTRUMENT WITH ROTATABLE AND ARTICULATABLE SURGICAL END EFFECTOR; U.S. patent application Ser. No. 16/885,838, entitled ELECTROSURGICAL INSTRUMENT WITH ASYNCHRONOUS ENERGIZING ELECTRODES; U.S. patent application Ser. No. 16/885,851, entitled ELECTROSURGICAL INSTRUMENT WITH ELECTRODES BIASING SUPPORT; U.S. patent application Ser. No. 16/885,860, entitled ELECTROSURGICAL INSTRUMENT WITH FLEXIBLE WIRING ASSEMBLIES; U.S. patent application Ser. No. 16/885,866, entitled ELECTROSURGICAL INSTRUMENT WITH VARIABLE CONTROL MECHANISMS; U.S. patent application Ser. No. 16/885,870, entitled ELECTROSURGICAL SYSTEMS WITH INTEGRATED AND EXTERNAL POWER SOURCES; U.S. patent application Ser. No. 16/885,873, entitled ELECTROSURGICAL INSTRUMENTS WITH ELECTRODES HAVING ENERGY FOCUSING FEATURES; U.S. patent application Ser. No. 16/885,879, entitled ELECTROSURGICAL INSTRUMENTS WITH ELECTRODES HAVING VARIABLE ENERGY DENSITIES; U.S. patent application Ser. No. 16/885,881, entitled ELECTROSURGICAL INSTRUMENT WITH MONOPOLAR AND BIPOLAR ENERGY CAPABILITIES; U.S. patent application Ser. No. 16/885,888, entitled ELECTROSURGICAL END EFFECTORS WITH THERMALLY INSULATIVE AND THERMALLY CONDUCTIVE PORTIONS; U.S. patent application Ser. No. 16/885,893, entitled ELECTROSURGICAL INSTRUMENT WITH ELECTRODES OPERABLE IN BIPOLAR AND MONOPOLAR MODES; U.S. patent application Ser. No. 16/885,900, entitled ELECTROSURGICAL INSTRUMENT FOR DELIVERING BLENDED ENERGY MODALITIES TO TISSUE; U.S. patent application Ser. No. 16/885,917, entitled CONTROL PROGRAM ADAPTATION BASED ON DEVICE STATUS AND USER INPUT; U.S. patent application Ser. No. 16/885,923, entitled CONTROL PROGRAM FOR MODULAR COMBINATION ENERGY DEVICE; and U.S. patent application Ser. No. 16/885,931, entitled SURGICAL SYSTEM COMMUNICATION PATHWAYS.

Applicant of the present application owns related U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety.

Applicant of the present application owns related U.S. patent application Ser. No. 16/887,493, filed May 29, 2020 and titled METHOD OF OPERATING A COMBINATION ULTRASONIC/BIPOLAR RF SURGICAL DEVICE WITH A COMBINATION ENERGY MODALITY END-EFFECTOR, the disclosure of which is hereby incorporated by reference in its respective entirety.

Before explaining various forms of surgical devices in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions utilized herein have been chosen for the purpose of describing the illustrative forms for the convenience of the reader and are not for the purpose of limitation thereof. As used herein, the term "surgical device" is used interchangeably with the term "surgical instrument." Furthermore, as used herein "ultrasonic blade" includes an component configured to delivery energy at a frequency configured to cut a tissue sample. However, it shall be appreciated that according to some aspects, an ultrasonic blade can be further configured for use as an electrode to deliver and/or receive RF energy, depending on the desired implementation.

Further, it is understood that any one or more of the following-described forms, expressions of forms, examples, can be combined with any one or more of the other following-described forms, expressions of forms, and examples.

Various forms are directed to improved ultrasonic and/or electrosurgical (RF) instruments configured for effecting tissue treating, dissecting, cutting, and/or coagulation during surgical procedures. In one form, a combined ultrasonic and electrosurgical device may be configured for use in open surgical procedures, but has applications in other types of surgery, such as minimally invasive laparoscopic, orthoscopic, or thoracoscopic procedures, for example, non-invasive endoscopic procedures, either in hand held or and robotic-assisted procedures. Versatility is achieved by selective application of multiple energy modalities simultaneously, independently, sequentially, or combinations thereof. For example, versatility may be achieved by selective use of ultrasonic and electrosurgical energy (e.g., monopolar or bipolar RF energy) either simultaneously, independently, sequentially, or combinations thereof.

In one aspect, the present disclosure provides an ultrasonic surgical clamp apparatus comprising an ultrasonic blade and a deflectable RF electrode such that the ultrasonic blade and deflectable RF electrode cooperate to effect sealing, cutting, and clamping of tissue by cooperation of a clamping mechanism of the apparatus comprising the RF electrode with an associated ultrasonic blade. The clamping mechanism includes a pivotal clamp arm which cooperates with the ultrasonic blade for gripping tissue therebetween. The clamp arm is preferably provided with a clamp tissue pad (also known as "clamp arm pad") having a plurality of axially spaced gripping teeth, segments, elements, or individual units which cooperate with the ultrasonic blade of the end-effector to achieve the desired sealing and cutting effects on tissue, while facilitating grasping and gripping of tissue during surgical procedures.

In one aspect, the end-effectors described herein comprise an electrode. In other aspects, the end-effectors described herein comprise alternatives to the electrode to provide a compliant coupling of RF energy to tissue, accommodate pad wear/thinning, minimize generation of excess heat (low coefficient of friction, pressure), minimize generation of sparks, minimize interruptions due to electrical shorting, or combinations thereof. The electrode is fixed to the clamp jaw at the proximal end and is free to deflect at the distal end. Accordingly, throughout this disclosure the electrode may be referred to as a cantilever beam electrode or as a deflectable electrode.

In other aspects, the end-effectors described herein comprise a clamp arm mechanism configured to apply high pressure between a pad and an ultrasonic blade to grasp and seal tissue, maximize probability that the clamp arm electrode contacts tissue in limiting or difficult scenarios, such as, for example, thin tissue, tissue under lateral tension, tissue tenting/vertical tension especially tenting tissue away from clamp arm.

In other aspects, the end-effectors described herein are configured to balance match of surface area/current densities between electrodes, balance and minimize thermal conduction from tissue interface, such as, for example, impacts lesion formation and symmetry, cycle time, residual thermal energy.

In other aspects, the end-effectors described herein are configured to minimize sticking, tissue adherence (minimize anchor points) and may comprise small polyimide pads.

In various aspects, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In various aspects, the end-effector comprises electrode biasing mechanisms.

In one general aspect, the present disclosure is directed to a method for using a surgical device comprising a combination of ultrasonic and advanced bipolar RF energy with a movable RF electrode on at least one jaw of an end-effector. The movable RF electrode having a variable biasing force from a proximal end to a distal end of the movable RF electrode. The movable RF electrode being segmented into discrete portions than can be put in electrical communication or isolated from each other. The movable RF electrode being made of a conductive or partially conductive material. It will be appreciated that any of the end effectors described in this disclosure may be configured with an electrode biasing mechanism.

In one aspect, the present disclosure provides a limiting electrode biasing mechanism to prevent ultrasonic blade to electrode damage. Generally, in various aspects, the present disclosure provides an end-effector for use with a ultrasonic/RF combination device, where the end-effector comprises an electrode. In one aspect, the combination ultrasonic/bipolar RF energy surgical device comprises an electrode biasing mechanism. In one aspect, the limiting electrode biasing mechanism is configured to prevent or minimize ultrasonic blade to electrode damage. The electrode is fixed to the clamp jaw at the proximal end and is free to deflect at the distal end. Accordingly, throughout this disclosure the electrode may be referred to as a cantilever beam electrode or as a deflectable electrode.

In various aspects, the present disclosure provides an electrode cantilever beam fixated at only one end comprising a biasing threshold mechanism. In one aspect, the deflectable cantilever electrode is configured for combination ultrasonic/bipolar RF energy surgical devices.

In one aspect, the combination ultrasonic/RF energy surgical device comprises an ultrasonic blade, a clamp arm, and at least one electrode which crosses over the ultrasonic blade. In one aspect, the electrode is configured to be deflectable with respect to the clamp arm and includes features to change the mechanical properties of the tissue under compression between the electrode and the ultrasonic blade. In another aspect, the electrode includes a feature to prevent inadvertent contact between the electrode and the ultrasonic blade to prevent or minimize ultrasonic blade to electrode damage.

In various aspects, the electrode comprises a metallic spring element attached at a proximal end of the clamp jaw of the end effector. The metallic spring element defines openings for receives therethrough one or more clamp arm pads (also known as "tissue pads" or "clamp tissue pads") and comprises integrated minimum gap elements. This configuration of the electrode provides a method of preventing tissue from accumulating around the biasing mechanism that can impact the performance of the electrode. This configuration also minimizes the binding between the wear pads and the biasing spring, increases the strength of the electrode to clamp arm connection, minimizes inadvertent release of the clamp arm pads by attaching the polyimide pads to the electrode, and balance matches the surface area/current densities between electrodes. The electrode is fixed to the clamp jaw at the proximal end and is free to deflect at the distal end. Accordingly, throughout this disclosure the electrode is deflectable and may be referred to as a cantilever beam electrode or deflectable electrode.

Although ultrasonic and radio frequency ("RF") energy surgical devices provide numerous surgical benefits, the unwanted sticking of tissue samples to clamp arm pads after clamping and/or sealing can be problematic. For example, if a tissue sample sticks to the ultrasonic or RF blade after a cutting and/or sealing operation, subsequent charring can occur due to an undesired, prolonged application of heat to the stuck tissue sample. Various clamp pads and clamp pad configurations have been contemplated to define a desired energy path and reduce the probability of unwanted sticking, such as those disclosed in U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety.

However, to further reduce tissue sticking to the ultrasonic and/or RF energy blade after a desired delivery of energy, it would be desirable to administer a specifically configured burst of energy to essentially kick the blade off the tissue sample. Accordingly, there is a need for devices, systems, and methods for automatically providing a small amount of specifically configured (e.g., amount, duration, frequency, etc.) energy to the blade after a surgical device performs a desired surgical operation (e.g., cutting or sealing), to remove the tissue sample from the blade and thus, reduce the probability of unwanted sticking and charring. It would be additionally beneficial if the administered energy could be automatically delivered at a particularly desirable moment after a surgical operation. For example, the specifically configured burst of energy could be automatically administered upon the opening of jaws of the surgical device, after the surgical operation is performed.

Referring now to FIG. 1, a surgical device 100 is depicted in accordance with at least one aspect of the present disclosure. According to the non-limiting aspect of FIG. 1, the surgical device 100 can include a housing 102 that defines a handle 104 in the form of a pistol grip. The housing 102 can further include a trigger 106 that, when squeezed, can be received into an internal cavity defined by the housing 102 and more specifically, the handle 104. The trigger 106 can be configured to operate a clamp arm 111 portion of an end effector 110 coupled to the housing 102 via a shaft 108, which can be rotated via a knob 122. The end effector 110 can include a clamp arm 111 and a blade 116, wherein the clamp arm 111 includes a clamp jaw 112, an electrode 118, and a clamp arm pad 120. The clamp jaw 112 can be pivotally movable about a pivot point 114. It shall be appreciated that the surgical device 100 of FIG. 1 is merely illustrative and that present disclosure contemplates other non-limiting aspects wherein the surgical device 100 has varying structural and electrical configurations. As such, the housing 102, trigger 106, clamp arm 111, and/or clamp jaw 112 configuration of FIG. 1 can be modified according to user preference and/or intended application.

According to one non-limiting one aspect, the clamp arm pad 120 can be made of a non-stick lubricious material such as PTFE or similar synthetic fluoropolymers of tetrafluoroethylene. PTFE is a hydrophobic, non-wetting, high density and resistant to high temperatures, and versatile material and non-stick properties. The clamp arm pad 120 can be electrically non-conductive. In contrast, the electrode 118 can be made of an electrically conductive material to deliver electrical energy such as monopolar RF, bipolar RF, microwave, or irreversible electroporation (IRE), for example. The electrode 118 can further include one or more gap setting pads made of a polyimide material, and in one aspect, can be made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted herein below, the clamp arm pads and gap pads described herein below are made of the materials described in this paragraph.

In further reference to FIG. 1, the electrode 118 and blade 116 can be coupled to a generator 133. The generator 133 can be configured to drive RF, microwave, and/or IRE energy to the electrode 118. The generator 133 can also be configured to drive an ultrasonic transducer acoustically coupled to the blade 116. In certain implementations, the electrode 118 can be one pole of an electrical circuit and the blade 116 can be the opposite pole of the electrical circuit. The housing 102 can include a switch 124 to activate the blade 116. According to some non-limiting aspects, the circuit can be contained in the housing 102. However, according to other non-limiting aspects, the circuit can reside in the generator 133. According to the non-limiting aspect of FIG. 1, the surgical device 100 can be coupled to the generator 133 via a cable 131 that conducts signals for the operation of the surgical device 100. In various aspects, the surgical device 100 can be configured to deliver at least two energy types (e.g., ultrasonic, monopolar RF, bipolar RF, microwave, or irreversible electroporation) to tissue located in the end effector 110 between the clamp arm 111 and the blade 116.

According to the non-limiting aspect of FIG. 1, the surgical device 100 can include one or more switches 124, 126, 130 to control and/or select a desired mode of the surgical device 100. For example, the housing 102 of the surgical device 100 can include a first activation button switch 126 for activating energy and a second "mode" button switch 130 for selecting an energy mode for the activation button switch. The second button switch 130 can be connected to a circuit that uses at least one input parameter to define the energy mode. The input parameter can be modified remotely through connection to a generator and/or through a software update. The energy mode can then be displayed on a user interface 128 communicably coupled to the surgical device 100. For example, can toggle through modes of the surgical device 100 by pressing the "mode" button switch 130 and a colored light on the user interface 128 can indicate which mode the user has currently selected. According to other non-limiting aspects, the generator 133 can provide an appropriate generator tone once a particular mode is selected.

Still referring to the non-limiting aspect of FIG. 1, the "mode" selection button switch 130 can be placed symmetrically on both sides of the housing 102. This can enable both right-handed and left-handed surgeons to toggle through modes of the surgical device 100 without requiring the use of a second hand. According to this non-limiting aspect, the "mode" selection button switch 130 can toggle in many different directions, which can enable the surgeon to select from a list of options and navigate more complex selections remotely from the sterile field without having to ask a circulator to make adjustments at the generator 133. The lighted indicator on the user interface 128 of the surgical device 100, in addition to generator 133 tones, can provide the surgeon feedback on which mode is selected through activation of the button switch 130.

In further reference to FIG. 1, the surgical device can further include a sensor 140 electrically coupled to a control circuit 150, 152. According to some non-limiting aspects, the control circuit 150 can be positioned within the housing 102. However, according to other non-limiting aspects, a control circuit 152 can be positioned within the generator 133. The sensor 140 can be configured to detect when the clamp jaw 112 is open and/or closed and generate signals associated an opened and/or closed status of the clamp jaw 112. According to some non-limiting aspects, the sensor 140 can be positioned such that it can monitor and detect a relative position of the trigger 106 and thus, the operation of the clamp arm 111 portion of an end effector 110. Such signals can be transmitted to the control circuit 150, 152. For example, the sensor 140, in conjunction with the control circuit 150, 152, can determine whether the jaws are still closed for the transmission of ultrasonic and/or RF energy, or if the trigger 106, or a closure switch, has been opened, signifying that the user is trying to release the tissue sample from the clamp jaws 112.

Figure 2:
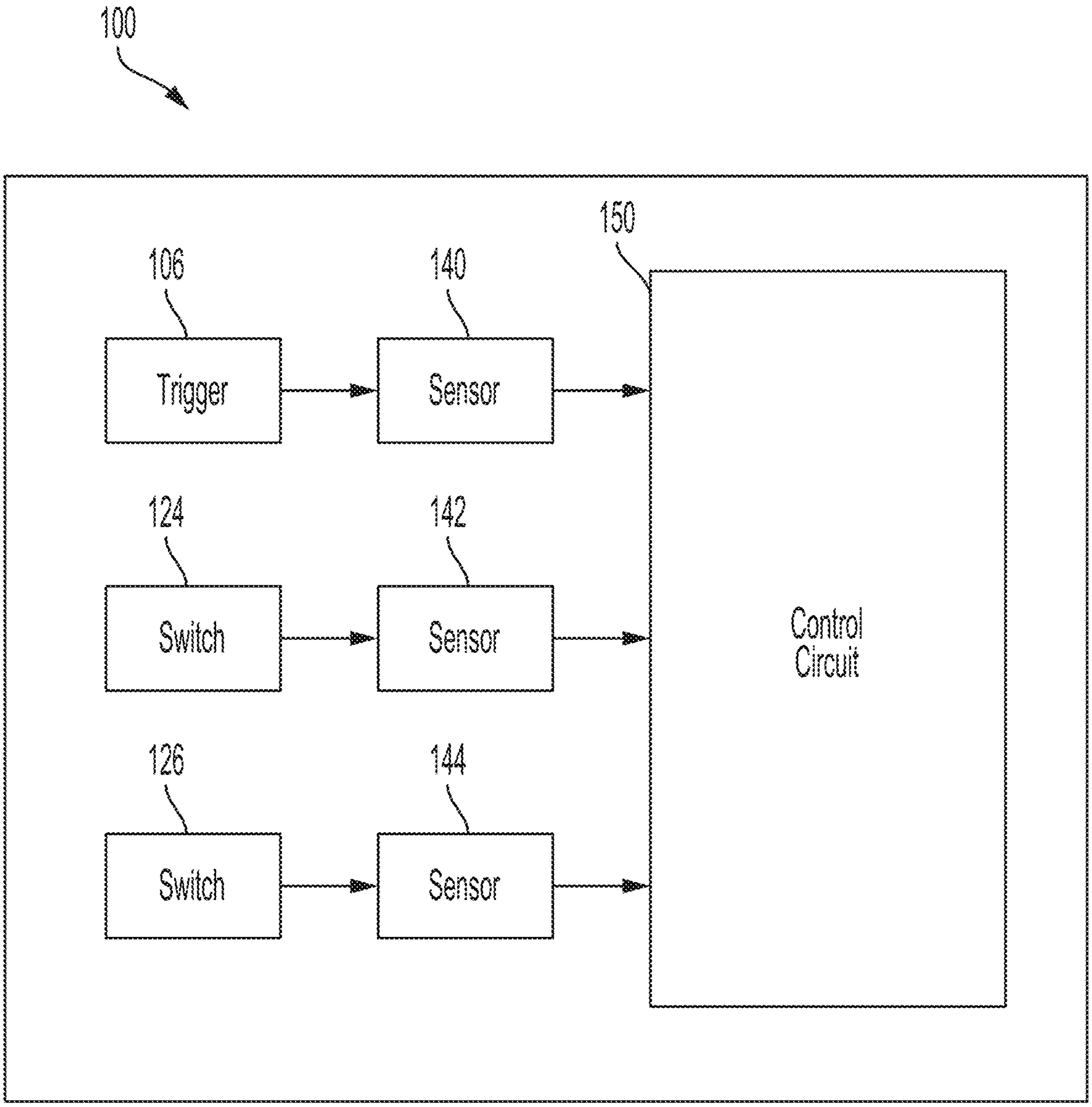
FIG. 2 illustrates an block diagram of one control circuit configuration of the surgical device of FIG. 1, in accordance with at least one aspect of the present disclosure.
Figure 3:
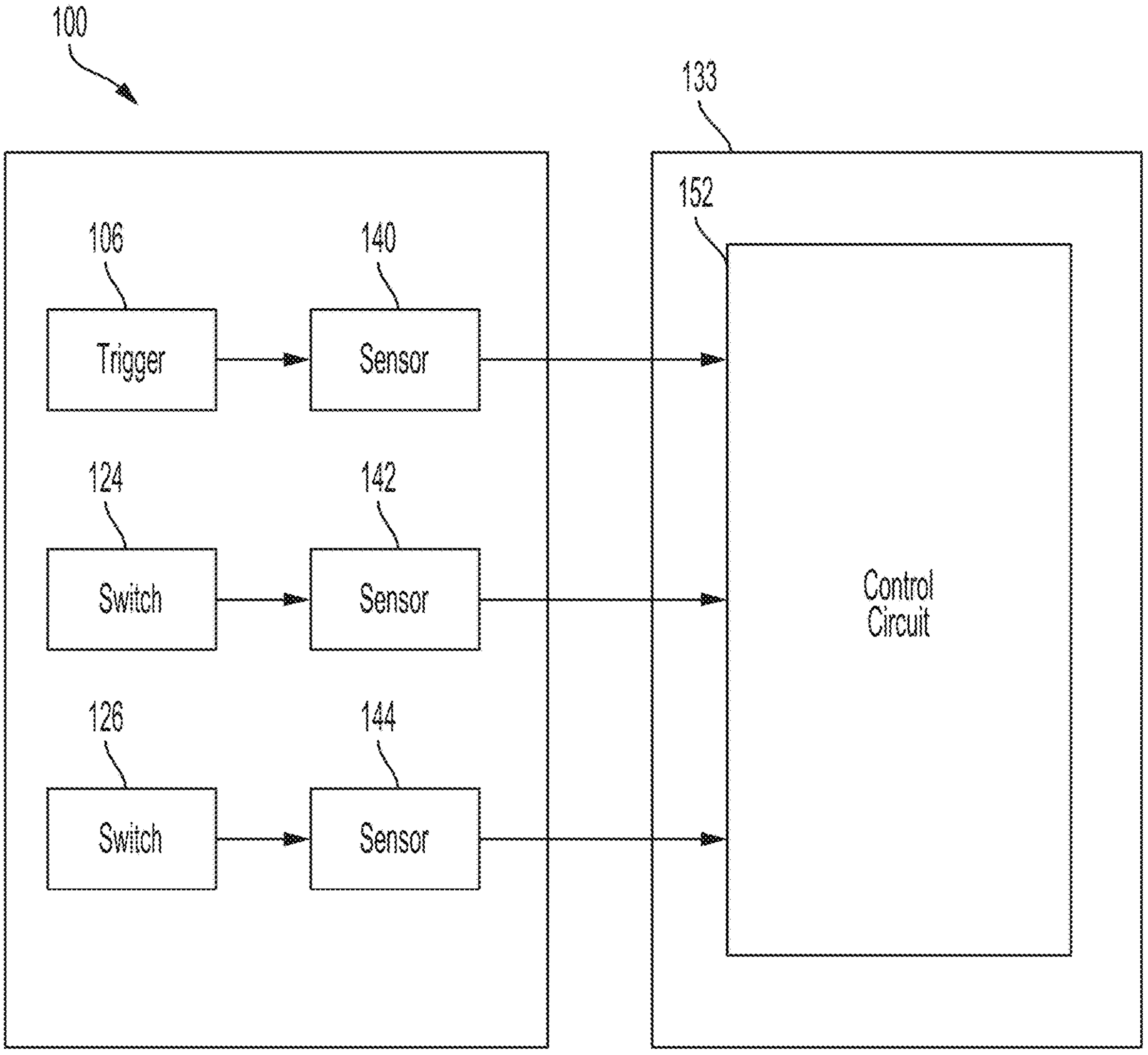
FIG. 3 illustrates an block diagram of another control circuit configuration of the surgical device of FIG. 1, in accordance with at least one aspect of the present disclosure.

Referring now to FIGS. 2 and 3, block diagrams illustrating several control circuit 150, 152 configurations of the surgical device 100 of FIG. 1 are depicted in accordance with at least one aspect of the present disclosure. According to the non-limiting aspect of FIG. 2, a control circuit 150 can be positioned within the housing 102 of the surgical device 100. The control circuit 150 can be electrically coupled to one or more sensors 140, 142, 144 configured to detect one or more switches 124, 126 and/or triggers 106 within the surgical device 100 and thus, can control the surgical device 100 in response to inputs received from the user via the switches 124, 126 and/or trigger 106. For example, the control circuit 150 can be electrically coupled to a sensor 140 configured to monitor and detect a relative position of the trigger 106 and thus, determine whether the jaws are closed for the transmission of energy, or if the user has initiated the opening of the clamp jaws 112 to release the tissue sample. Likewise, the sensors can detect and monitor switch 124 and/or switch 126, generate and transmit signals associated with the relative positions of those switches 124, 126 such that the control circuit 150 can determine whether a user wants to activate or deactivate RF energy or activate or deactivate the blade 116.

According to the non-limiting aspect of FIG. 3, a control circuit 152 can be positioned within the generator 133 while remaining electrically coupled to the surgical device 100. Nonetheless, the sensors 140, 142, 144 remain positioned within the housing 102 of the surgical device 100 and configured to detect one or more switches 124, 126 and/or triggers 106 within the surgical device 100 and thus, the control circuit 152 can still control the surgical device 100 in response to inputs received from the user via the switches 124, 126 and/or trigger 106. For example, the control circuit 152 can once again be electrically coupled to a sensor 140 configured to monitor and detect a relative position of the trigger 106 and thus, can determine whether the jaws are closed for the transmission of energy, or if the user has initiated the opening of the clamp jaws 112 to release the tissue sample. Likewise, the sensors can detect and monitor switch 124 and/or switch 126, generate and transmit signals associated with the relative positions of those switches 124, 126 such that the control circuit 152 can determine whether a user wants to activate or deactivate RF energy or activate or deactivate the blade 116.

Figure 4:
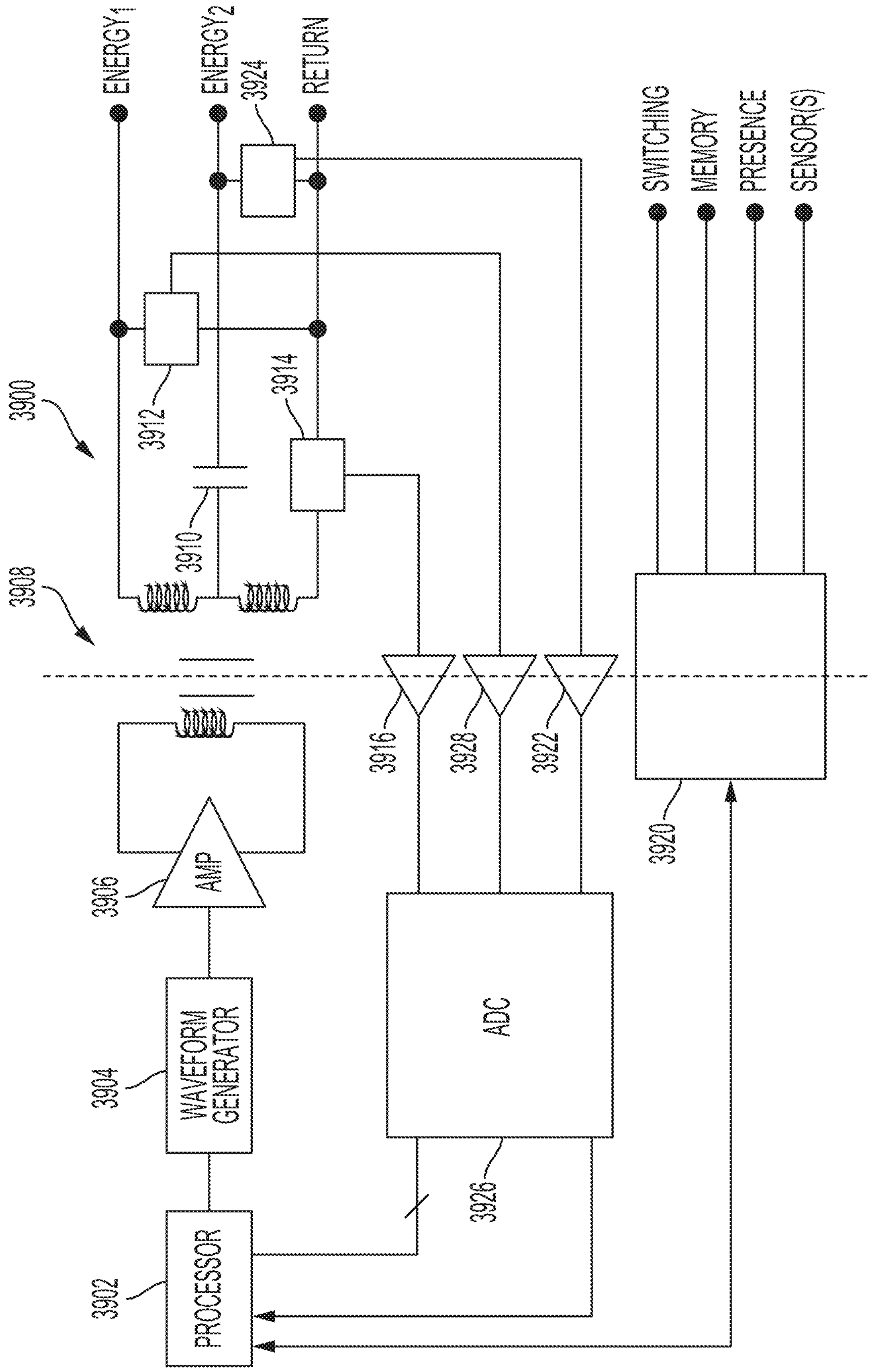
FIG. 4 illustrates a circuit diagram of a generator configured for use with the surgical device of FIG. 1, in accordance with at least one aspect of the present disclosure.

Referring now to FIG. 4, a circuit diagram of a generator 3900 configured for use with the surgical device 100 of FIG. 1 is depicted in accordance with at least one aspect of the present disclosure. According to the non-limiting aspect of FIG. 4, the generator 3900 can be configured to drive ultrasonic, RF energy, and/or multiple energy modalities to the surgical device 100. The generator 3900 can provide RF and ultrasonic signals for delivering energy to a surgical device 100 either independently, in combination, serially, and/or simultaneously, according to user preference and/or intended application.

In further reference to FIG. 4, at least one output of the generator 3900 can deliver multiple energy modalities (e.g., ultrasonic, bipolar RF, monopolar RF, irreversible electroporation, reversible electroporation, and/or microwave energy, etc.) through a single port. These outputs can be configured for delivery to the end effector to be administered to the tissue for treatment. The generator 3900 can include a control circuit that, according to the non-limiting aspect of FIG. 4, can be processor 3902 coupled to a waveform generator 3904. The processor 3902 and waveform generator 3904 can be configured to generate a variety of signal waveforms based on information stored in a memory coupled to the processor 3902. Digital information associated with a waveform can be provided to the waveform generator 3904 which can include one or more digital-to-analog converter ("DAC") circuits, which can be configured to convert the digital input into an analog output. The analog output can then be fed to an amplifier 3906 for signal conditioning and amplification. The conditioned and amplified output of the amplifier 3906 can be coupled to a power transformer 3908. The signals can be coupled across the power transformer 3908 to a secondary side, which can be a patient isolation side. For example, a first signal of a first energy modality can be provided to the surgical device 100 between the terminals labeled $ENERGY_1$ and RETURN. A second signal of a second energy modality can be coupled across a capacitor 3910 and can be provided to the surgical device 100 between the terminals labeled $ENERGY_2$ and RETURN. It shall be appreciated that more than two energy modalities can be output and that the subscript "n" can be superimposed on on the output designations such that the generator 3900 can produce up to $ENERGY_n$ outputs across "n" terminals. Here, "n" is a positive integer greater than 1. It also will be appreciated that up to "n" return paths $RETURN_n$ can be provided without departing from the scope of the present disclosure.

A first voltage sensing circuit 3912 can be coupled across the terminals labeled $ENERGY_1$ and the RETURN path to measure the output voltage therebetween. A second voltage sensing circuit 3924 can be coupled across the terminals labeled $ENERGY_2$ and the RETURN path to measure the output voltage therebetween. A current sensing circuit 3914 can be disposed in series with the RETURN leg of the secondary side of the power transformer 3908 as shown to measure the output current for either energy modality. If different return paths are provided for each energy modality, then a separate current sensing circuit should be provided in each return leg. The outputs of the first and second voltage sensing circuits 3912, 3924 can be provided to respective isolation transformers 3916, 3922 and the output of the current sensing circuit 3914 can be provided to another isolation transformer 3918. The outputs of the isolation transformers 3916, 3928, 3922 in the on the primary side of the power transformer 3908 (non-patient isolated side) can be provided to a one or more ADC circuit 3926. The digitized output of the ADC circuit 3926 can be provided to the processor 3902 for further processing and computation. The output voltages and output current feedback information can be employed to adjust the output voltage and current provided to the surgical device 100 and to compute output impedance, among other parameters. Input/output communications between the processor 3902 and patient isolated circuits can be provided through an interface circuit 3920. Sensors, such as the sensors 140, 142, 144 can also be in electrical communication with the processor 3902 by way of the interface circuit 3920.

In one aspect, the impedance can be determined by the processor 3902 by dividing the output of either the first voltage sensing circuit 3912 coupled across the terminals labeled $ENERGY_1$/RETURN or the second voltage sensing circuit 3924 coupled across the terminals labeled $ENERGY_2$/RETURN by the output of the current sensing circuit 3914 disposed in series with the RETURN leg of the secondary side of the power transformer 3908. The outputs of the first and second voltage sensing circuits 3912, 3924 are provided to separate isolations transformers 3916, 3922 and the output of the current sensing circuit 3914 is provided to another isolation transformer 3916. The digitized voltage and current sensing measurements from the ADC circuit 3926 are provided the processor 3902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 93 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 3912 by the current sensing circuit 3914 and the tissue impedance may be measured by dividing the output of the second voltage sensing circuit 3924 by the current sensing circuit 3914.

As shown in FIG. 4, the generator 3900 comprising at least one output port can include a power transformer 3908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 3900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 3900 can be steered, switched, or filtered to provide the frequency to the end effector of the surgical device 100. The connection of an ultrasonic transducer to the generator 3900 output would be preferably located between the output labeled ENERGY1 and RETURN as shown in FIG. 4. In one example, a connection of RF bipolar electrodes to the generator 3900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details regarding the generator 3900 of FIG. 4 are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is hereby incorporated by reference in its entirety.

Figure 5A:
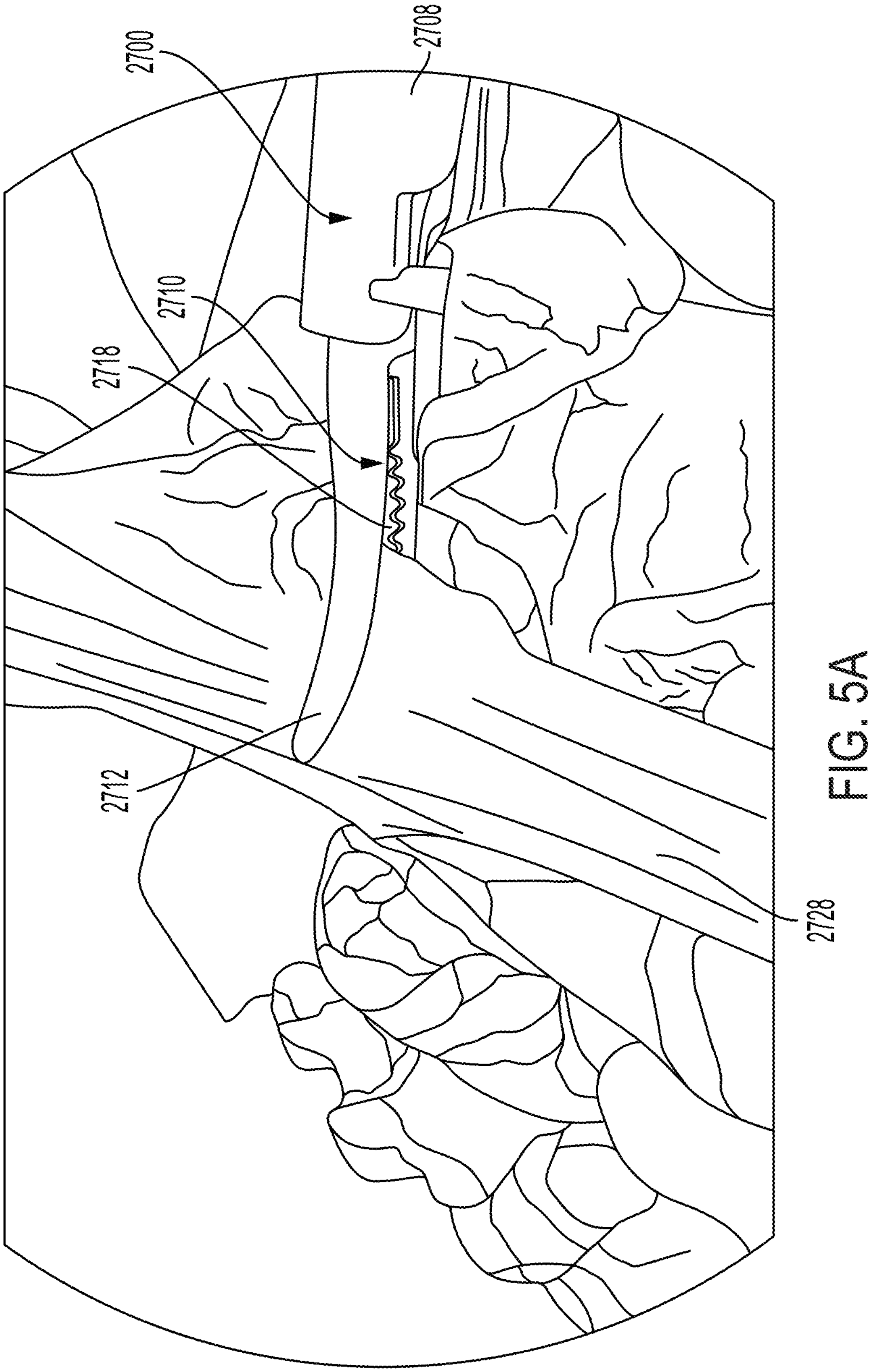
FIGS. 5A-5C, illustrate another surgical device in use during a surgical procedure, in accordance with at least one non-limiting aspect of the present disclosure.
Figure 5B:
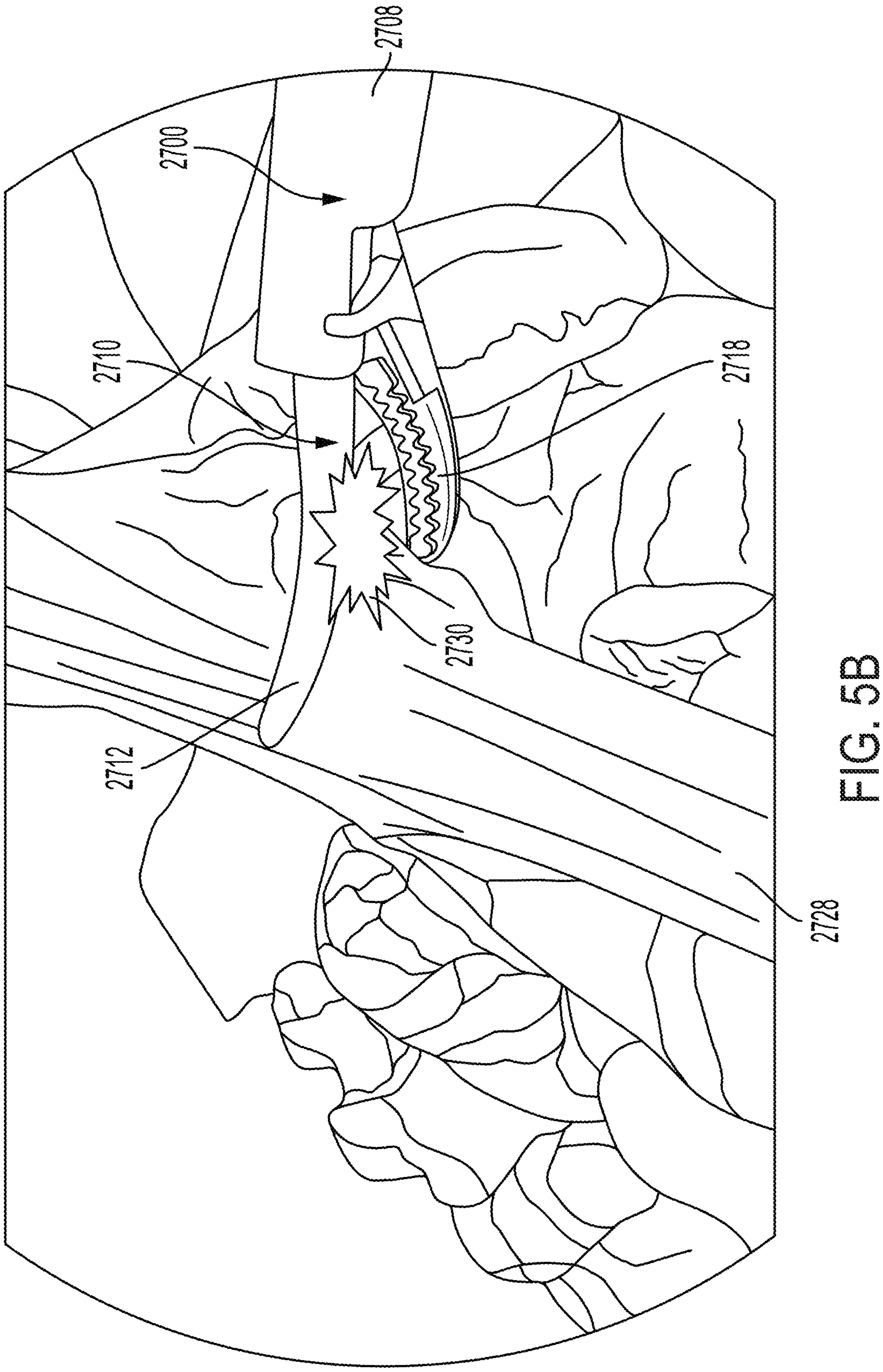

Referring now to FIGS. 5A-5B, several illustrations of another surgical device 2700 in use during a surgical procedure are depicted in accordance with at least one non-limiting aspect of the present disclosure. According to the non-limiting aspect of FIGS. 5A-5C, the surgical device 2700 can be similarly configured to the surgical device 100 of FIG. 1, such that the surgical device 2700 can reduce tissue sample 2728 (e.g., a blood vessel, etc.) sticking to one or more clamp jaws 2712 of the surgical device 2700 after energy is administered by a source of electrosurgical and/or RF energy, such as the generator 133 of FIG. 1. For example, according to the non-limiting aspect of FIGS. 5A-5C, the surgical device 2700 can include a housing that defines a handle in the form of a pistol grip. The housing can further include a trigger (not shown) that, when squeezed, can operate one or more clamp jaws 2712 on an end effector 2710 coupled to the housing via a shaft 2708, similar to the trigger 106 of FIG. 1.

According to the non-limiting aspect of FIG. 5A, a desired surgical operation (e.g., cutting, sealing, etc.) can be performed on the tissue sample 2728, which can be clasped between the one or more clamp jaws 2712 of the surgical device 2700. After the desired surgical operation (e.g., cutting, sealing, etc.) is performed, the surgical device 2700—and more specifically, a sensor (e.g., sensor 140 of FIGS. 2 and 3) positioned within the surgical device 2700—can monitor and detect a relative position of the trigger. As such, when the surgical operation is complete and a user of the surgical device 2700 releases the trigger to open the one or more clamp jaws 2712 and release the tissue sample 2728, the sensor can detect the release of the trigger and transmit a signal associated with the release of the trigger to a control circuit (e.g. control circuits 150, 152 of FIGS. 2 and 3).

In response to the signal received from the sensor, the control circuit can cause the generator to administer an amount, such as a burst, of energy 2730 particularly configured to cause the tissue sample 2728 to be released from the one or more clamp jaws 2712 of the surgical device 2700, as depicted in FIG. 5B. The burst of energy 2730 can configured to include a specific frequency based on a cold frequency and/or a measured ultrasonic frequency during a previous activation. In other words, a duration and/or other parameters (e.g., magnitude, frequency, amplitude, etc.) associated with the burst of energy 2730 administered to the tissue 2728 can be alternately configured relative to the energy used during the surgical operation, itself, such that the burst of energy 2730 neither cuts nor seals the tissue 2728. Instead, the burst of energy 2730 can overcoming any friction and/or adhering forces between the tissue sample 2728 and the one or more clamp jaws 2712 that arose during the surgical operation. For example, the burst of energy 2730 can include a small amount of ultrasonic energy imparted for a small duration of time (e.g., less than 0.5 seconds, etc.) that will physically separate the tissue sample 2728 from the one or more clamp jaws 2712. For example, it could be preferable to configure the burst of energy 2730 can include a ultrasonic pulse of a duration greater than or equal to 0.1 second and less than or equal to 1 second.

According to other non-limiting aspects, the burst of energy 2730 can include a ultrasonic pulse can be administered at a specific transducer current set point and/or a desired percentage of a current set point. For example, it could be preferable to configure the burst of energy 2730 to include a ultrasonic pulse greater than or equal to 50% and less than or equal to 120% of the current set point. A lower percentage of the current set point can be preferable in cases where the burst of energy 2730 is used in conjunction with a non-stick coating and/or clamp pad, such as those described in U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety.

In other words, the burst of energy 2730 can be particularly configured to jolt the tissue out of the one or more clamp jaws 2712 after the surgical operation, that the tissue 2728 does not stick, thereby mitigating the risk of the tissue 2728 charring. Although the non-limiting aspect of FIGS. 5A-5C contemplates the automatic administration of the burst of energy 2730 via a sensor and control circuit, according to other non-limiting aspects, the burst of energy 2730 can be alternately and/or additionally administered via user activation of a button positioned on the housing of the surgical device 2700. In still other non-limiting aspects, the surgical device 2700 can reduce a "time to find" lock and thus, allow for the administration of the burst of energy 2730. Furthermore, a time delay can be added between closure switch open and start of the ultrasonic pulse if the closure switch opening occurs after the RF activation is finished. Such a delay can reduce the likelihood of inadvertent activation while still partially clamped on tissue. For example, the time delay can be less than or equal to 0.5 seconds, although any time can be selected in accordance with user preference and/or intended application.

Additionally and/or alternately, a control circuit of the surgical device 2700 can be programmed such that the burst of energy 2730 will not be administered, altered, or will be cut short in a variety of scenarios. For example, the burst of energy 2730 will not be administered or will be cut short if the user manually initiates firing before and/or during an automatic administration of the burst of energy 2730. Alternately and/or additionally, if the user activates the surgical device 2700 during the automatic administration of the burst of energy 2730, the control circuit could cause the generator to directly adjust a parameter of the burst of energy 2730 until the energy is suitable for performing the surgical operation without terminating the firing. Alternately, the control circuit surgical device 2700 According to other non-limiting aspects, such adjustments can be made if the user closes the jaws again before and/or during the automatic administering of the burst of energy 2730.

Figure 5C:
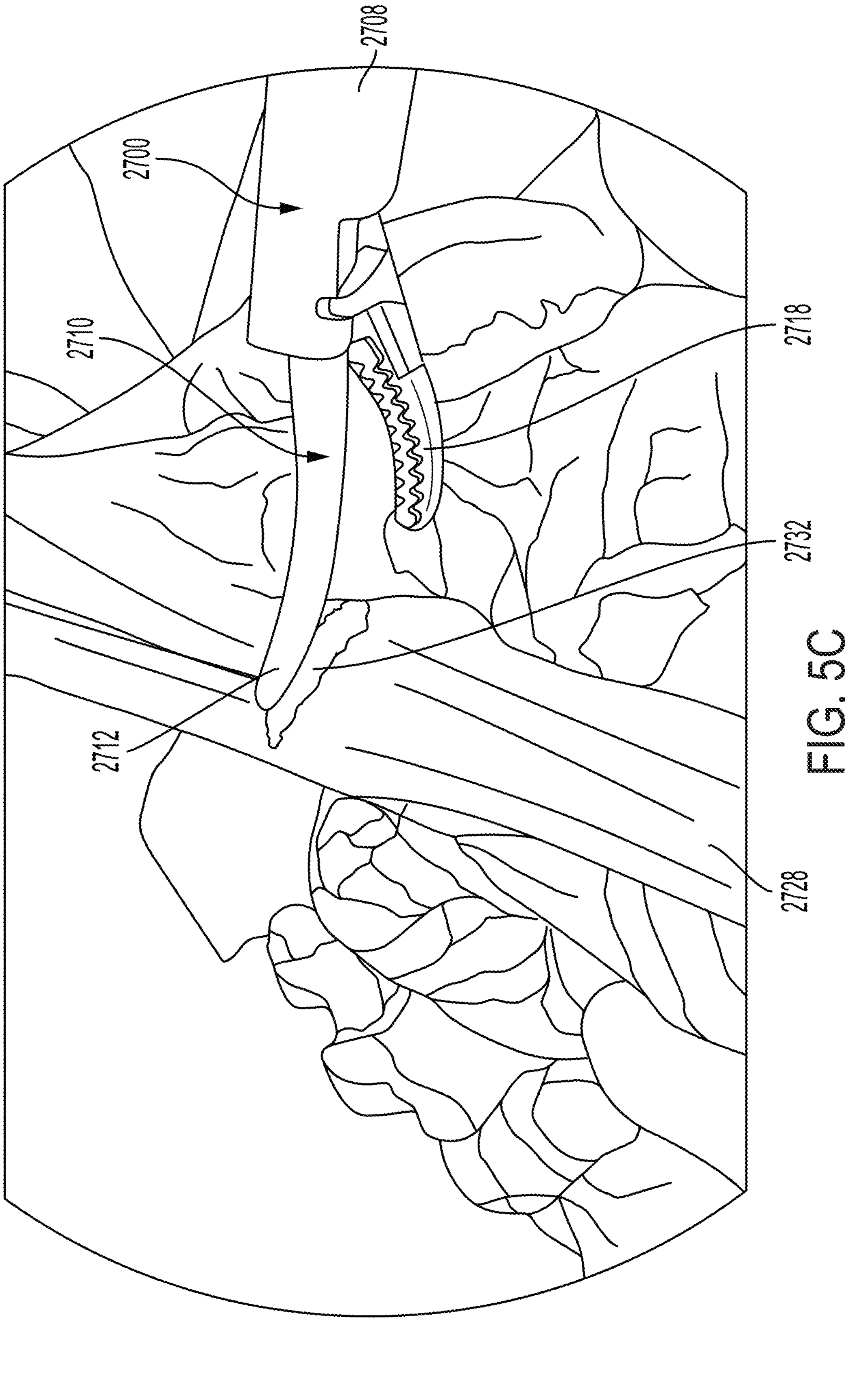

Accordingly, the surgical device 2700 of FIGS. 5A-5C can be implemented to ensure that a portion 2732 of the tissue 2728 that was operated on is either cut and/or sealed in accordance with a surgical object, without any adverse or unintended effect caused by unwanted sticking and or charring of the tissue sample 2728 to the one or more clamp jaws 2712, as depicted in FIG. 5C. Moreover, the administration of the burst of energy 2730 (FIG. 5B) can be automatic, since the sensor and control circuit can collectively monitor the trigger and thus, the intention of the user to release the tissue 2728 from the one or more clamp jaws 2712. After the burst of energy 2728 and subsequent release of the tissue sample 2728 from the one or more clamp jaws 2712, the user can easily remove the end effector 2710 from the tissue sample 2728. Although the non-limiting aspect of FIGS. 5A-5C depict a particularly configured surgical device 2700 and a particular type and form of tissue 2728, it shall be appreciated that, according to other non-limiting aspects, the surgical device 2700 can be alternately configured and can be used to perform a surgical operation on alternate types and forms of tissue. Furthermore, the burst of energy 2730 can be automatically administered even if the one or more clamp jaws 2712 were never fully closed, or were opened while the surgical operation was being performed.

Figure 6:
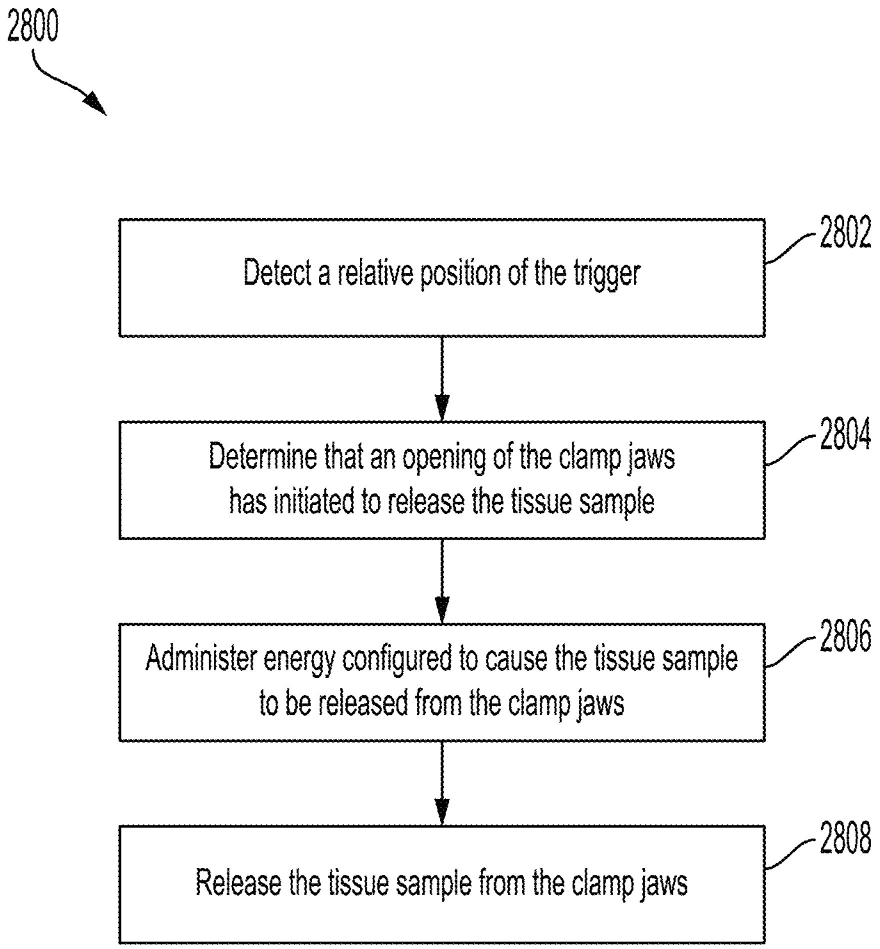
FIG. 6 illustrates a logic flow diagram of a method of using a surgical device, in accordance with at least one non-limiting aspect of the present disclosure.

Referring now to FIG. 6, a logic flow diagram of a method 2800 of using a surgical device is depicted in accordance with at least one non-limiting aspect of the present disclosure. According to the non-limiting aspect of FIG. 6, the method 2800 can include detecting 2802, via a sensor (e.g., sensor 140 of FIGS. 2 and 3) of the surgical device a relative position of the closure trigger (e.g., trigger 106 of FIG. 1). The method 2800 can further include determining 2804, via a control circuit (e.g. control circuits 150, 152 of FIGS. 2 and 3) of the surgical device, that the user has initiated the opening of the clamp jaws to release the tissue sample. Thus, the method 2800 can further include administering 2806, via the control circuit of the surgical device, a burst of energy configured to cause the tissue sample to be released from the clamp jaws. Finally, the method 2800 can further include releasing 2808 the tissue sample from the clamp jaws of the surgical device. Of course, the steps of the method 2800 of FIG. 6 are non-exclusive and thus, the method 2800 can include additional steps. For example, the method 2800 can be modified to include any other functions performed by the surgical devices, generators, end effectors, control circuits, and/or sensors, amongst other components disclosed herein.

As previously discussed, various clamp pads and clamp pad configurations have been contemplated to define a desired energy path and reduce the probability of unwanted sticking, such as those disclosed in U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety. Such clamp arms can be used to administer the previously-discussed bursts of energy. However, clamp arms and clamp arm pads can degrade, break, and wear out due to continued use of an implementing surgical device. This is particularly important when clamp arm pads are implemented to reduce the risk of tissue sticking and charring, since such pads provide the non-stick surface that interfaces with a tissue sample. This degradation can be exacerbated when the clamp arm construction utilizes different materials, including, but not limited to, Teflon (e.g., PTFE, etc.), aluminum (e.g., 60601 T0, etc.), and/or stainless steel (e.g., 300 series, 17-4, H900, etc.). Accordingly, there is a need for means of reducing failure modes of clamp arm pads attachment of dissimilar materials implemented in end effectors—and more specifically, clamp pads—such as those disclosed in U.S. patent application Ser. No. 16/951,259.

Figure 7:
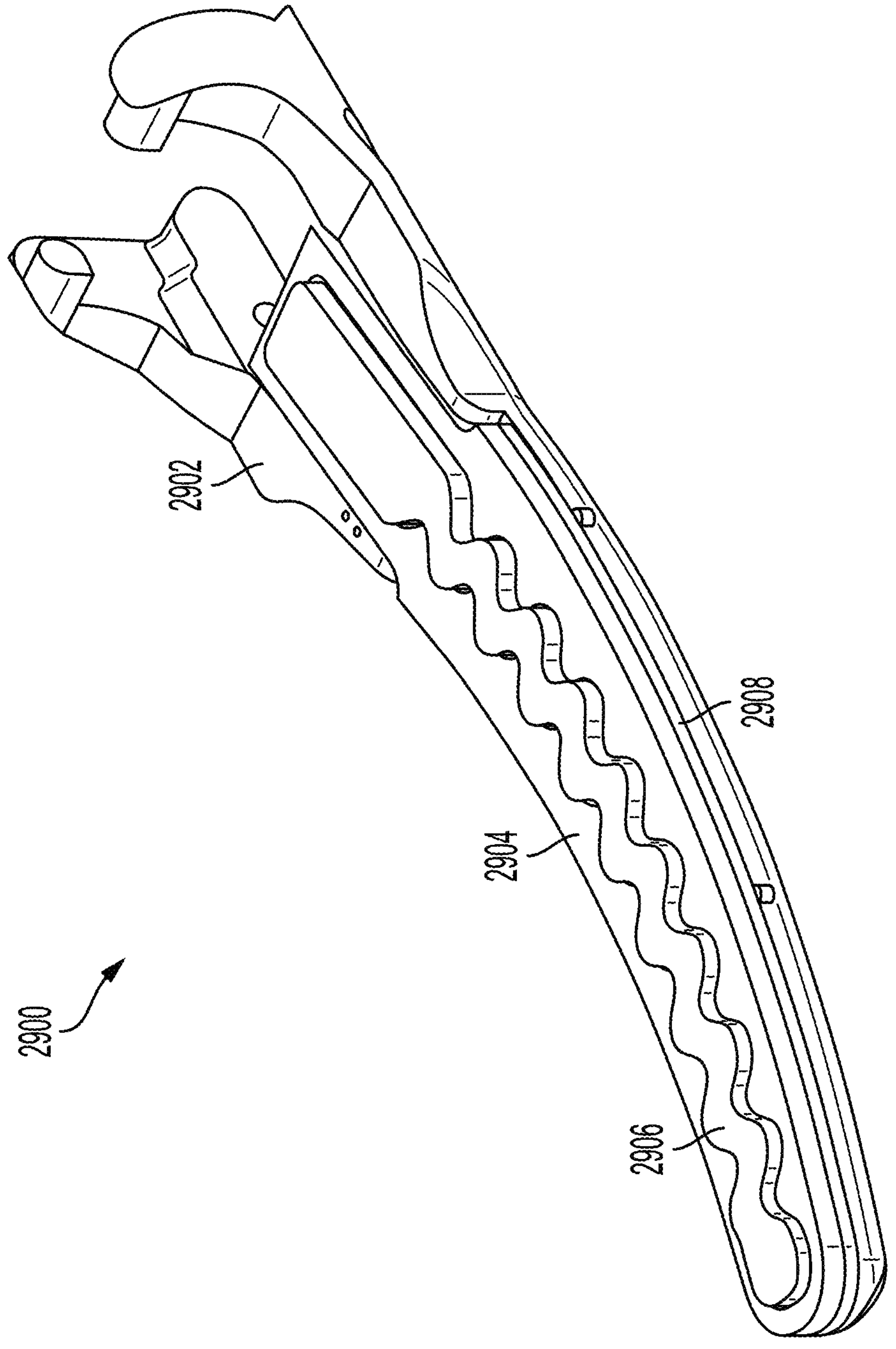
FIG. 7 illustrates a clamp arm configured for use with a surgical device, in accordance with at least one non-limiting aspect of the present disclosure.

Referring now to FIG. 7, a clamp arm 2900 or jaw including a soft electrode 2904 configured for use with a surgical device is depicted in accordance with at least one non-limiting aspect of the present disclosure. According to the non-limiting aspect of FIG. 7, the clamp arm 2900 can include a base 2902, an electrode 2904, a clamp arm pad 2906 configured to reduce sticking, and an intermediate material 2908 positioned between the electrode 2904 and a base 2902. The base 2902, electrode 2904, clamp arm pad 2906, and intermediate material 2908 can be constructed of different materials that are desirable for the intended function of those components. For example, according to the non-limiting aspect of FIG. 7, the base 2902 can be constructed from a stainless steel (e.g., 17-4, H900, etc.), the electrode 2904 can be constructed from aluminum (e.g., 60601 T0, etc.), the clamp arm pad 2906 can be constructed from a non-stick material (e.g., PTFE, etc.), and the intermediate material 2908 can be constructed from a different stainless steel (e.g., 300 series, etc.). When surgical devices and end effectors are configured to administer multiple forms of energy (e.g., ultrasonic, RF advanced bipolar, etc.), there is a need to preserve the non-stick pad 2906 to reduce the likelihood of tissue sticking to the electrode 2904. Furthermore, components of the end effector (e.g., an ultrasonic blade) contacts the metal clamp arm, it can cause heat, sparks, and can potentially result in broken blades.

In further reference to FIG. 7, the clamp arm 2900 can be configured to transfer energy to a clamped tissue sample while mitigating the aforementioned failure modes and mitigating degradation of the clamp arm pad 2906. According to the non-limiting aspect of FIG. 7, the electrode 2904 can be incorporated into the clamp arm 2900 and can be constructed of a material with a hardness configured to reduce excitation and degradation. For example, the electrode 2904 can be constructed from a material with a lower hardness than the material of other components, such as a ultrasonic blade. Accordingly, if the ultrasonic blade contacts the electrode, the harder blade will wear through the less hard electrode, without breaking the blade. In other words, the clamp arm 2900 of FIG. 7 can include a "soft" electrode that provides a risk mitigation. In non-limiting aspects where a blade-breakage algorithm is deployed, the soft electrode will preserve the blade if the blade-breakage detection algorithm fails. Some non-limiting examples of blade-breakage algorithms are described in U.S. patent application Ser. No. 16/144,335 titled METHODS FOR CONTROLLING TEMPERATURE IN ULTRASONIC DEVICE and U.S. patent application Ser. No. 16/144,383 titled METHODS FOR ESTIMATING AND CONTROLLING STATE OF ULTRASONIC END EFFECTOR, both of which were filed on Sep. 27, 2018 and the disclosures of which are hereby incorporated by reference in their entirety. Other non-limiting examples of blade-breakage algorithms are described in U.S. patent application Ser. No. 16/115,239 titled DETERMINING THE STATE OF AN ULTRASONIC ELECTROMECHANICAL SYSTEM ACCORDING TO FREQUENCY SHIFT and U.S. patent application Ser. No. 16/115,247 titled DETERMINING THE STATE OF AN ULTRASONIC END EFFECTOR, both of which were filed Aug. 28, 2018 and the disclosures of which are also hereby incorporated by reference in their entirety.

According to the non-limiting aspect of FIG. 7, the electrode 2904 can be constructed from relatively soft materials, such as pure titanium (e.g., Ti Grade 1, etc.), copper, and/or an annealed or T0-type aluminum (e.g., Al 6061 T0, Al 1100 annealed, ½ hard, etc.). For example, the electrode 2904 can be constructed from aluminum, which could be preferable due to its thermal and/or electrical conductivity, biocompatibility, and/or material availability. The soft electrode 2904 can be attached via any desirable attachment processes, such as welding, brazing, adhering (e.g., conductive, non-conductive), and/or soldering, amongst others. Soft electrodes 2904 can be easier to fabricate and assemble compared to conductive polymer or conductive PTFE materials. The soft metal electrode 2904 of FIG. 7 may also be more robust to repetitive usage than conductive surface treatments.

Figure 8A:
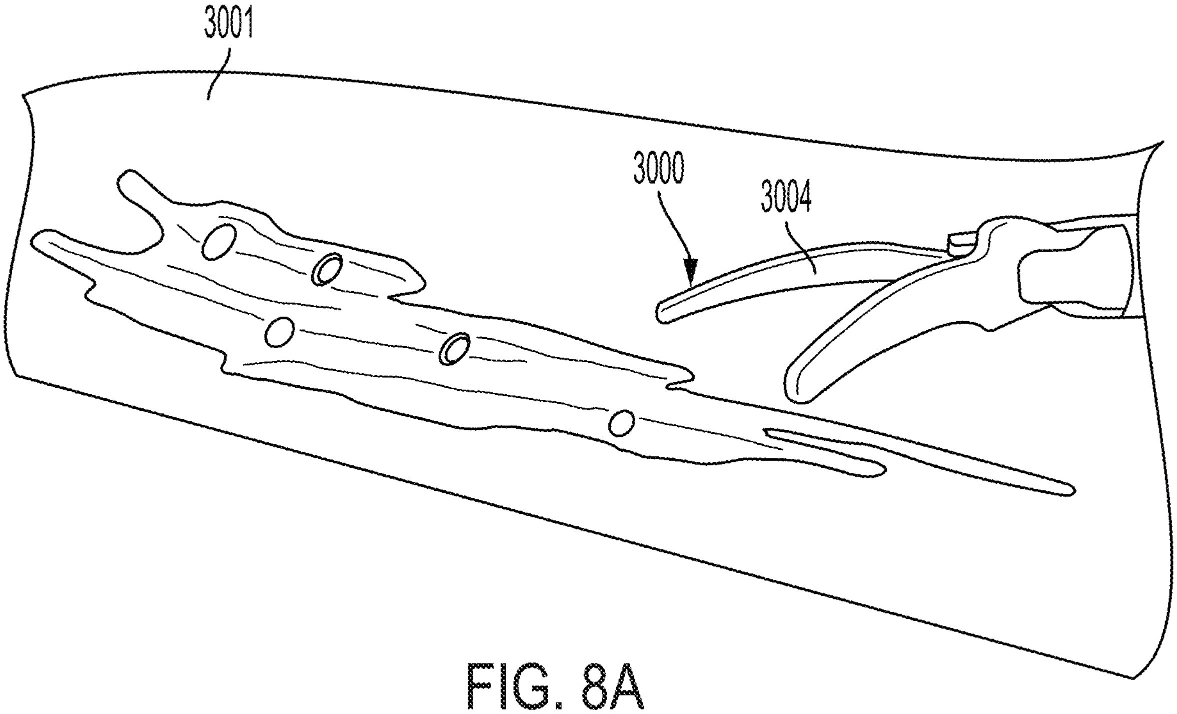
FIGS. 8A and 8B illustrate the result of clamp arms featuring different electrodes, in accordance with several non-limiting aspects of the present disclosure.
Figure 9A:
FIGS. 9A-9E illustrate the experimental results of several clamp arms featuring various electrodes, in accordance with several non-limiting aspects of the present disclosure.
Figure 9B:
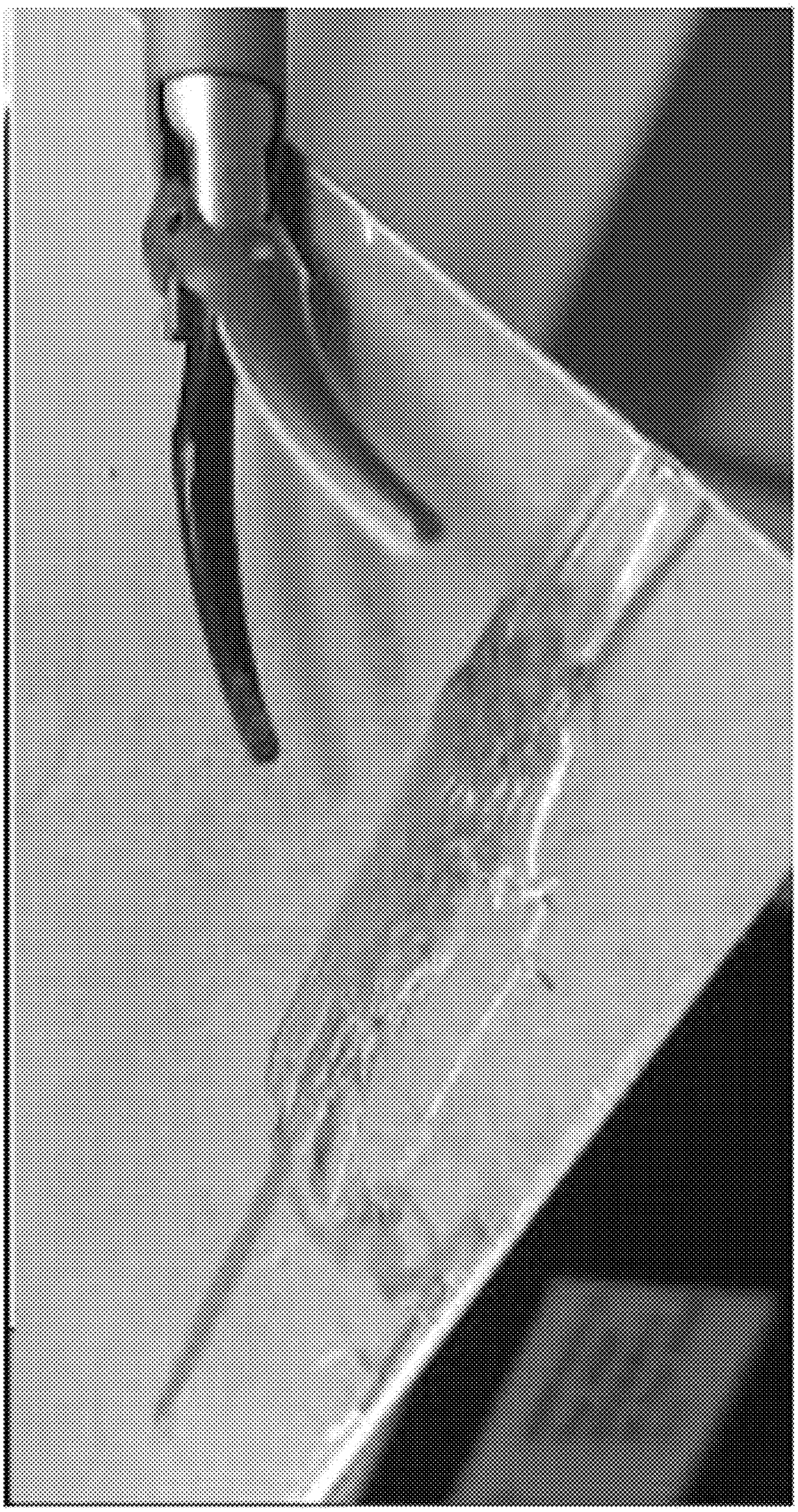
Figure 9C:
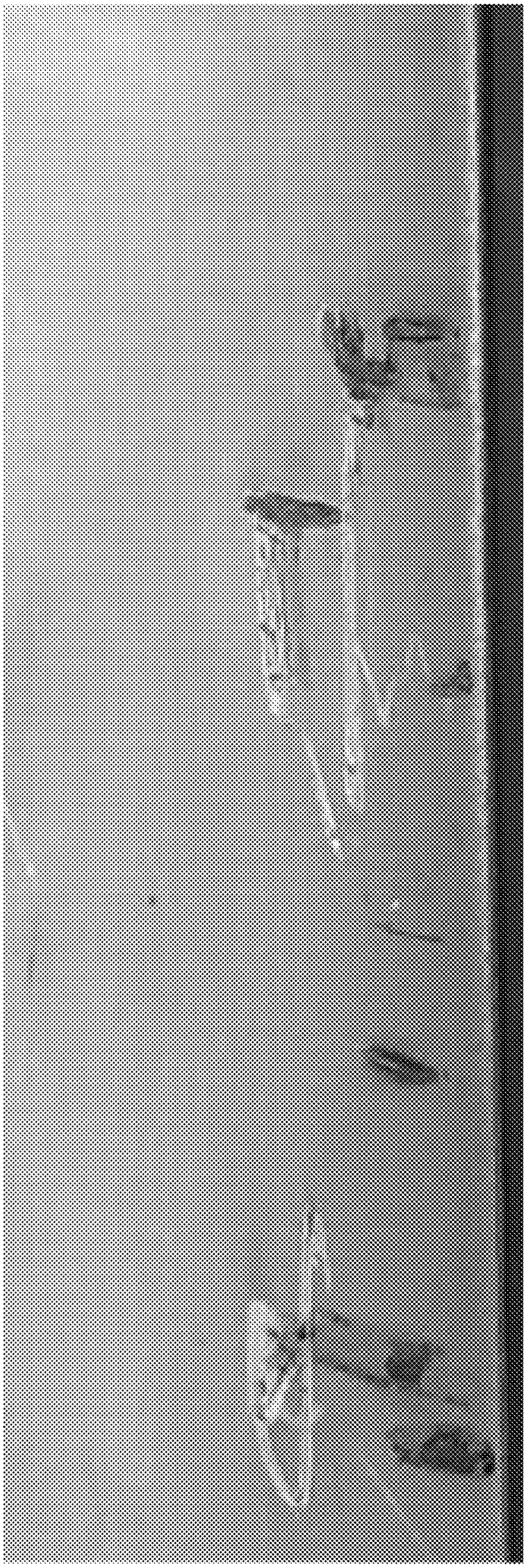

Referring now to FIGS. 9A-9D, the experimental results of several clamp arms featuring various electrodes are depicted in accordance with several non-limiting aspects of the present disclosure. According to the non-limiting aspect of FIG. 8A, the clamp arm 3000 can include an electrode 3004 constructed from a 300-series stainless steel (e.g., SS 304). This electrode 3004 produced a high-amount of sparks when it contacted a surface 3001 intended to simulate the construction of a ultrasonic blade. Moreover, material was removed from the surface 3001, indicating that the blade would have been damaged because it would have had a hardness that was less than the hardness of the electrode 3004. This is representative of other relatively hard materials that were tested for the electrode 3004. For example, FIGS. 9A, 9B, and 9C illustrate the results of a grade-two titanium 3120, a stainless steel 304 electrode 3130, and a stainless steel 330 electrode 3140, respectively, which also produced sparks, removed material from the blade, and in the case of stainless steel 330, the blade turned red, then blue, and then broke due to the heat generated by the electrode.

Figure 8B:
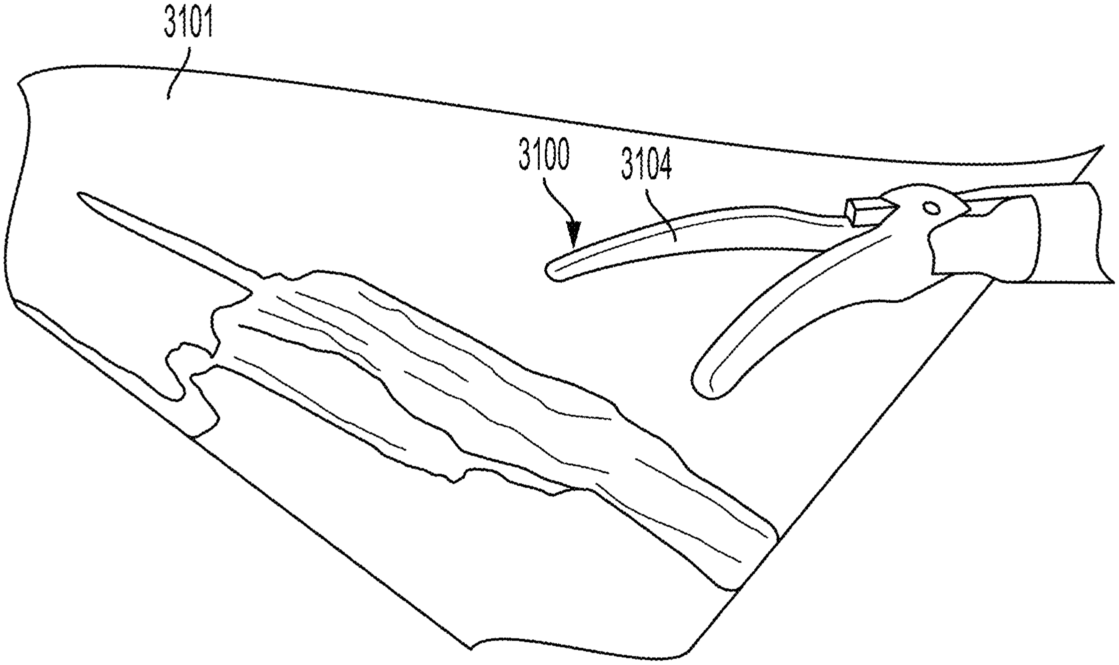
Figure 9D:
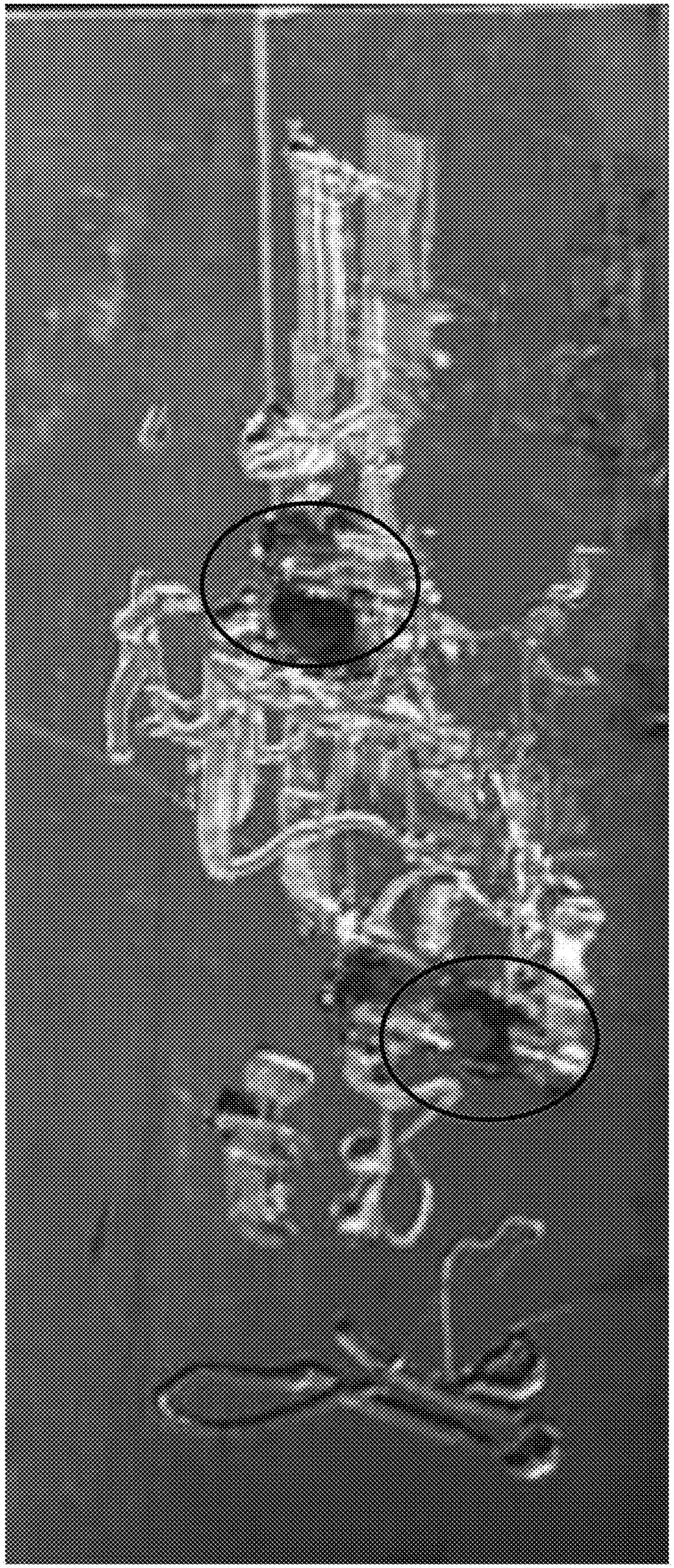
Figure 9E:
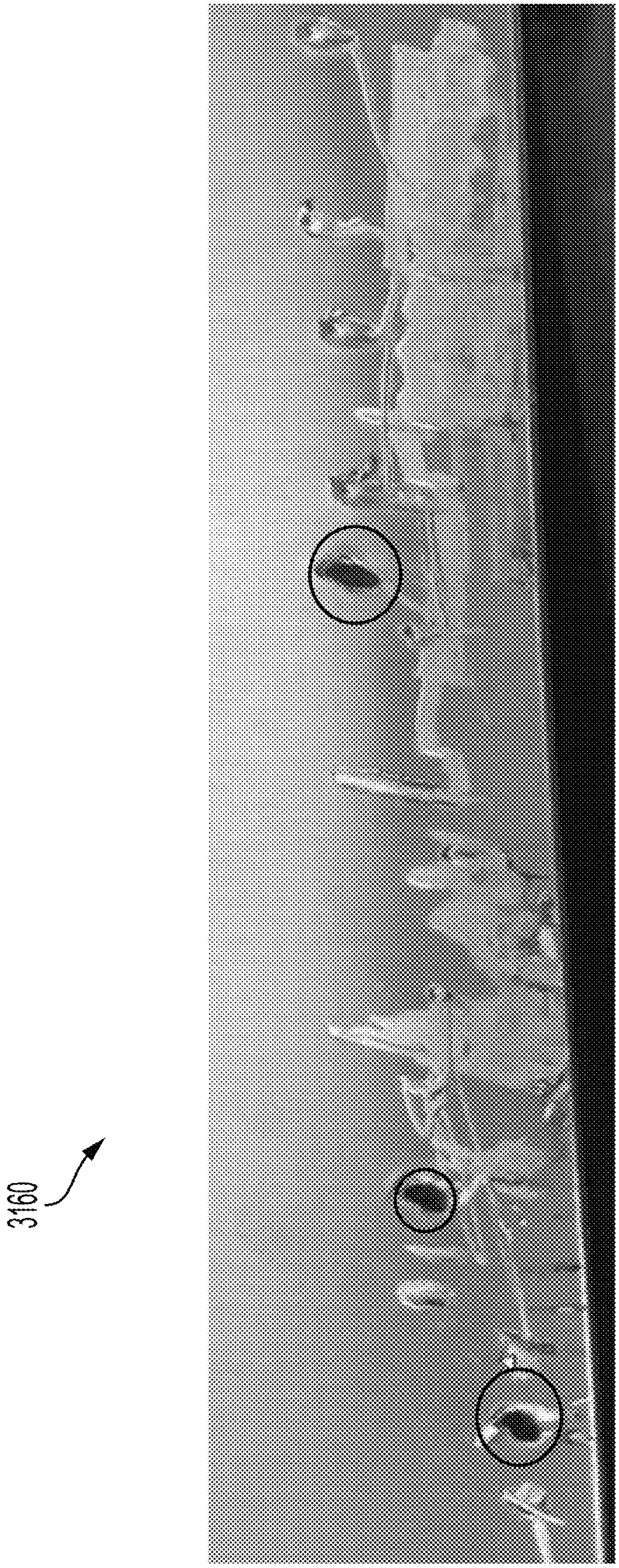

According to the non-limiting aspect of FIG. 8B, the clamp arm 3100 can include a soft electrode 3104 constructed from a copper (e.g., copper 110). The soft electrode 3104 produced a couple of sparks when it contacted a surface 3101 intended to simulate the construction of a ultrasonic blade. However, no material was removed from the surface 3001, indicating that the blade would not have been damaged because it would have had a hardness that was greater than the hardness of the soft electrode 3104. This is representative of other relatively soft materials that were tested for the soft electrode 3104. For example, FIG. 9D illustrates the results of a copper (e.g., copper 110) electrode 3150, which produced a couple sparks, and removed no material from the blade simulating surface 3101. For example, FIG. 9E illustrates the results of an aluminum (e.g., Al 6061-T0) electrode 3160, which produced no sparks, and removed no material from the blade simulating surface 3101.

Figure 10A:
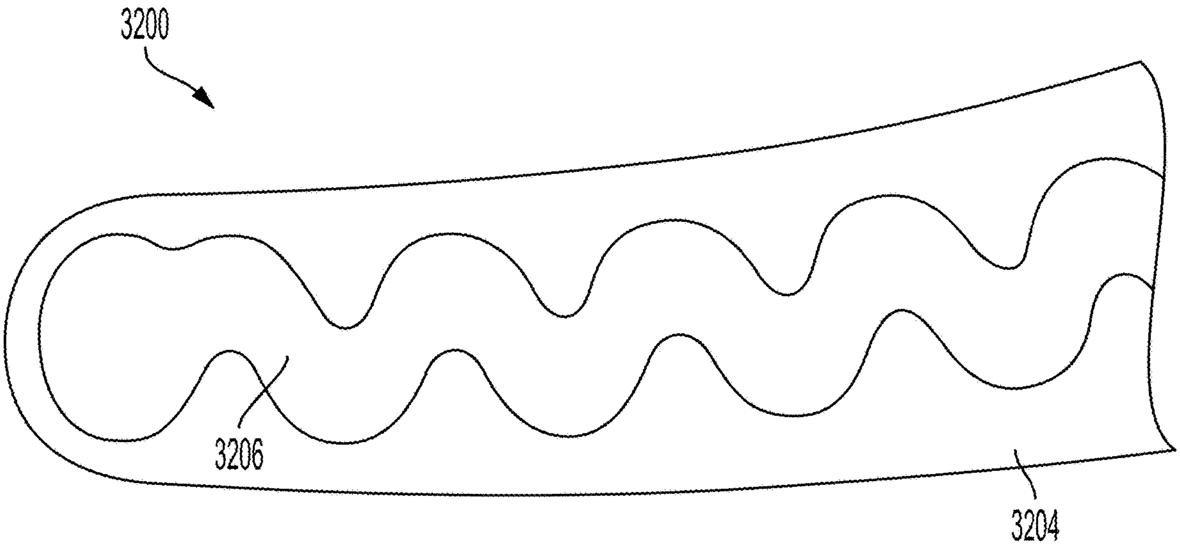
FIGS. 10A and 10B illustrate a clamp arm including a soft metal electrode, in accordance with at least one non-limiting aspect of the present disclosure.
Figure 10B:
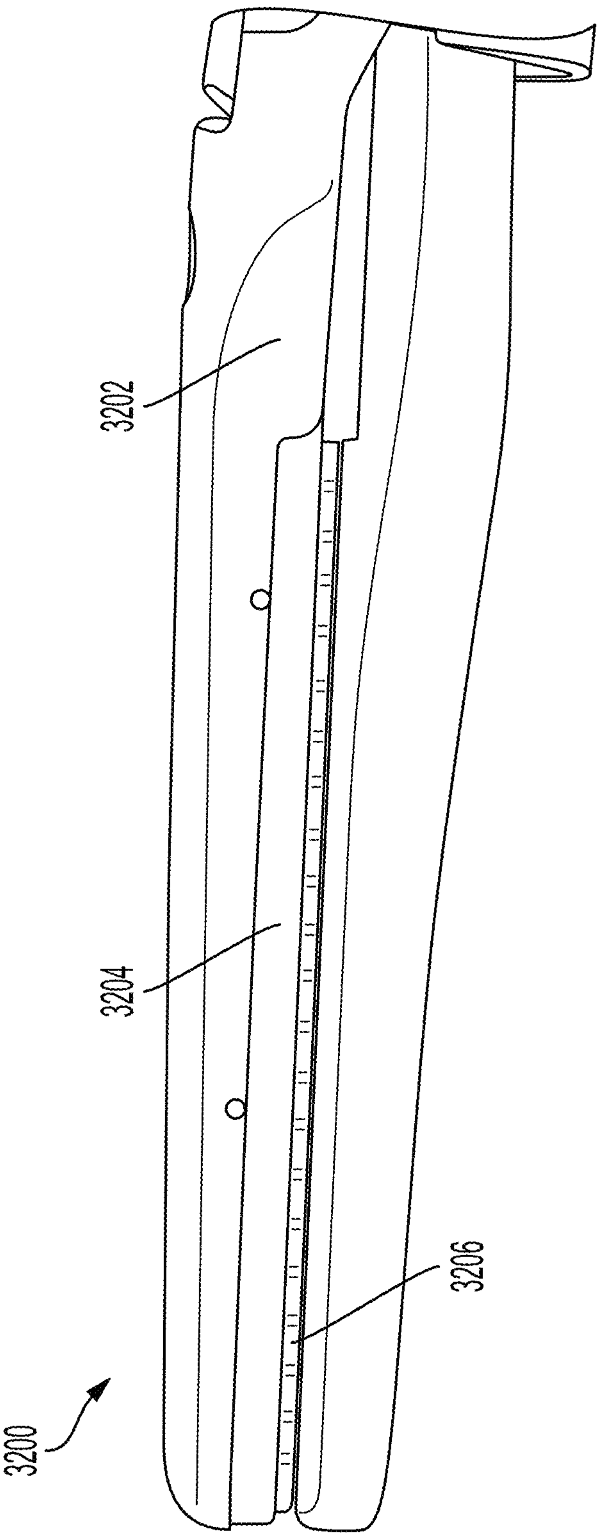

Referring now to FIGS. 10A and 10B, a clamp arm 3200 including a soft metal electrode 3204 is depicted in accordance with at least one non-limiting aspect of the present disclosure. According to the non-limiting aspect of FIGS. 10A and 10B, the soft metal electrode 3204 can be constructed from an aluminum, such as Al 6061, and can be epoxied to the clamp arm 3200. According to some non-limiting aspects, the soft metal electrode 3204 can be annealed. As such, the soft metal electrode 3204 can produce results, such as those illustrated in FIG. 9E. In other words, the soft metal electrode 3204 is not likely to produce sparks and is not likely to remove material from a blade, as simulated by the surface 3101 of FIG. 9E. As depicted in FIG. 10B, the soft metal electrode 3204 can be integrated into a base material 3202 and the non-stick clamp pad 3206 can be integrated within the electrode 3204.

As previously discussed, various clamp pads and clamp pad configurations have been contemplated to define a desired energy path and reduce the probability of unwanted sticking, such as those disclosed in U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety. However, such clamp pads can utilize different materials, such as Teflon (e.g., PTFE, etc.), aluminum (e.g., 60601 T0, etc.) and stainless steel (e.g., 17-4 PH, H900 HT, 300 series). However, multi-component assemblies involving dissimilar materials can result in insecure attachments, which can lead to further excitation and degradation of the non-stick clam pads discussed herein. Accordingly, there is also a need for means of providing a robust, secure attachment of dissimilar materials implemented in end effectors—and more specifically, clamp pads—such as those disclosed in U.S. patent application Ser. No. 16/951,259.

Figure 11:
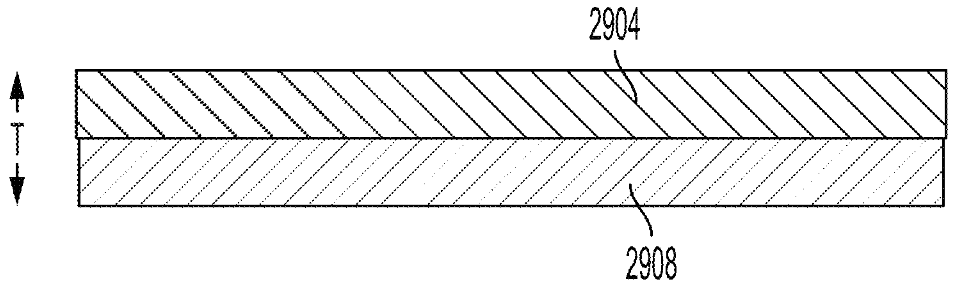
FIG. 11 illustrates a side view of an interface between the electrode and the intermediate material of the clamp arm of FIG. 7, in accordance with at least one non-limiting aspect of the present disclosure.

Referring now to FIG. 11, a side view of an interface between the electrode 2904 and the intermediate material 2908 of the clamp arm 2900 of FIG. 7 is depicted in accordance with at least one non-limiting aspect of the present disclosure. As previously discussed, the electrode 2904 can be constructed from aluminum (e.g., 60601 T0, etc.) and the intermediate material 2908 can be constructed from a different stainless steel (e.g., 300 series, etc.). In essence, the intermediate material 2908 can enhance the mechanical interface between the electrode 2904 and the base 2902 (FIG. 7), which can be constructed from a different type of stainless steel (e.g., 17-4, H900, etc.).

However, components constructed from different materials, such as the electrode 2904 and intermediate material 2908 of FIG. 11, can be difficult to attach using material bonding. For example, an electrode 2904 constructed from aluminum can be difficult to attach to an intermediate material 2908 constructed from stainless steel. Accordingly, the present disclosure contemplates a cladding process to adhere the electrode 2904 to the intermediate material 2908. In other words, cladding can be utilized to form bond the electrode 2904 and the intermediate material 2908, constructed of two or more distinct metals or alloys with differing properties, using a metallurgical bonding process. For example, the cladding process can utilize roll bonding and/or explosion bonding processes to bond the electrode 2904 to the intermediate material 2908.

Once clad, the bonded electrode 2904 and intermediate material 2908 can be formed into a desired geometrical configuration via a desired process (e.g., machining, wire electrical discharge machining ("EDM"), stamping, fine blanking, etc.). The electrode 2904 geometry should achieve a desired fit around the clamp arm pad 2906 (FIG. 7). For example, according to the non-limiting aspect of FIG. 7, the electrode 2904 is machined to define a serpentine-shaped cavity dimensionally configured to accommodate the serpentine-shaped clamp arm pad 2906 (FIG. 7). According to other non-limiting aspects, the geometric configuration can be altered in accordance with user preference and/or intended application. Once assembled, the intermediate material 2908, which can be constructed from a stainless steel, can be laser welded to the base 2902 (FIG. 7) of the clamp arm 2900 (FIG. 7) for a secure attachment.

According to the non-limiting aspect of FIG. 11, the clad electrode 2904 and intermediate material 2908 can be particular dimensioned to a desired thickness T. The thickness T can be particularly configured to achieve a desired electrode characteristic (e.g., life, resiliency, hardness, etc.). For example, the thickness T can range anywhere between 0.005 inches and 0.08 inches and, according to some non-limiting aspects, can be 0.025 inches thick. The electrode 2904 characteristics can be further tuned by apportioning the thickness T attributed to the electrode 2904 material and intermediate material 2908, as desired. According to the non-limiting aspect of FIG. 11, the total thickness T can be apportioned into equal portions of the electrode 2904 material and intermediate material 2908. For example, the electrode 2904 can have a thickness of approximately 0.013 inches and the intermediate material 2908 can have a thickness of approximately 0.012 inches. As such, the total thickness T of the clad assembly can have a tolerance, such as plus or minus 0.001 inch, for example. However, in other non-limiting aspects, the ratio is attenuated. It shall be appreciated that such dimensions and tolerances vary in other non-limiting aspects of the present disclosure. For example, adding additional electrode 2904 material (e.g., aluminum) can increase the amount of material of the clamp arm pad 2906 (FIG. 7) and thus, the clamp arm pad 2906 (FIG. 7) life. Alternately and/or additionally, increasing the amount of intermediate material 2908 (e.g., stainless steel) can improve the quality of the weld and can result in more robustness. Other suitable materials for the construction of the electrode 2904 and/or intermediate material 2908 can include zinc, 304 stainless steel (annealed to ½ hard), 60601 Aluminum (annealed to ½ hard), 5052 Aluminum (annealed to ¼ hard), and/or 1100 Aluminum (Annealed to ½ hard), amongst others.

Figure 12:
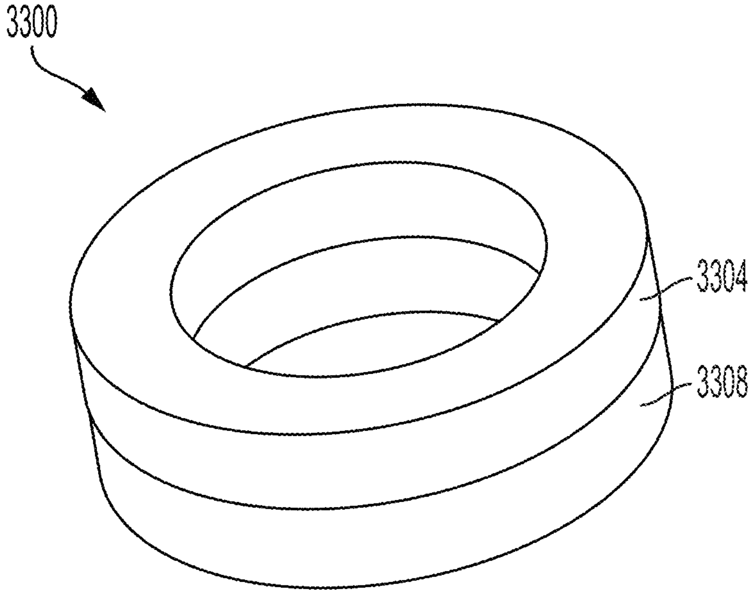
FIG. 12 illustrates a perspective view of another clad electrode, in accordance with at least one non-limiting aspect of the present disclosure.

Referring now to FIG. 12, a perspective view of another clad electrode 3300 is depicted in accordance with at least one non-limiting aspect of the present disclosure. According to the non-limiting aspect of FIG. 12, the clad electrode 3300 includes an electrode material 3304 that has been clad to an intermediate material 3308. Once again, the electrode 3304 can be constructed from aluminum (e.g., 60601 T0, etc.) and the intermediate material 3308 can be constructed from a different stainless steel (e.g., 300 series, etc.). However, unlike the elongated serpentine-shaped configuration of the electrode 2904 and intermediate material 2908 of FIG. 7, the clad electrode 3300 of FIG. 12 was machined to define a circular configuration. Of course, it shall be appreciated that the cladding techniques and constructions disclosed herein can be utilized to enhance the robustness of electrodes of varying geometric configurations.

Still referring to FIG. 12, the clad electrode 3300 has been dimensioned and configured to achieve desirable material properties. For example, the clad electrode 3300 of FIG. 12 can include a resistance to high-temperatures, no galvanic corrosion, and has a strong metallurgical bond between the electrode 3304 and the intermediate material 3308, which can enhance the secure attachment of the electrode 3304 to a clamp arm (not shown). The clad electrode 3300 achieves such properties without the use of interlayers and eliminates the need for mechanical fasteners, which can complicate the assembly process, add expenses, constrain the geometric configuration of the clad electrode 3300 by accommodating the fasteners, and result in a less secure connection.

Figure 13:
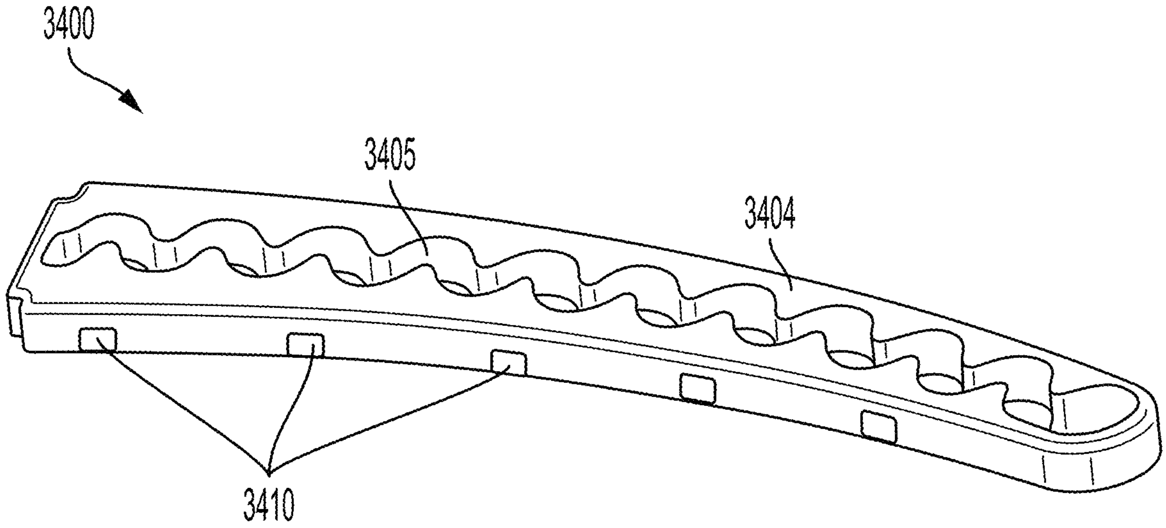
FIG. 13 illustrates a perspective view of another electrode, in accordance with at least one non-limiting aspect of the present disclosure.

Referring now to FIG. 13, a perspective view of another electrode 3400 is depicted in accordance with at least one non-limiting aspect of the present disclosure. Similar to the electrode 2904 of FIG. 7, the electrode 3400 of FIG. 13 can be machined to define a cavity 3405 configured to accommodate a clamp arm pad, such as the pad 3906 of FIG. 7. Although the cavity 3405 of FIG. 13 has a serpentine-shaped configuration, it shall be appreciated that, according to other non-limiting aspects, the electrode 3400 can be alternately configured to accommodate clamp arm pads of varying shapes and sizes. The electrode material 3404 of FIG. 13 can include aluminum (e.g., 6061 T0 aluminum), although the present disclosure contemplates other non-limiting aspects wherein the electrode material 3404 is selected from a variety of suitable materials. For example, zinc can also make a suitable electrode material 3404 for the construction of the electrode 3400.

However, unlike the electrodes 2904, 3304 of FIGS. 7 and 11, the electrode 3400 of FIG. 13 does not utilize a cladding process to enhance the attachment of the electrode 3400 to a clamp arm pad (not shown). Rather, the electrode 3400 of FIG. 13 can be manufactured to define one or more pockets 3410 configured to accommodate an intermediate material (not shown), such as the intermediate materials 2908, 3308 of FIGS. 7 and 11. For example, the intermediate material inserted in the one or more pockets 3410 can be a stainless steel configured to attach the electrode 3400 to a clamp arm via a laser weld process. However, according to other non-limiting aspects, other materials and means of attachment can be implemented to achieve the desired attachment. Although the non-limiting aspect of FIG. 12 depicts five pockets 3410 of an oval-type configuration, the number, size, and shape of the pockets 3410 are different in other non-limiting aspects.

According to the non-limiting aspect of FIG. 13, intermediate material (e.g., stainless steel) can be embedded within each of the one or more pockets 3410 using thermal spray technology, although the present disclosure contemplates other means of embedding the intermediate material into the pockets 3410. This reduces the amount of intermediate material necessary to achieve a secure attachment of the electrode 3400 to the clamp arm of the surgical device, allowing the amount of electrode material 3404 to be optimized compared to the non-limiting aspects of FIGS. 7 and 11. As such, the electrode 3400 of FIG. 13 can be suitable for increasing the amount of material for a clamp arm pad, such as the clamp arm pad 2906 of FIG. 7, which can increase the life of the clamp arm pad.

Figure 14:
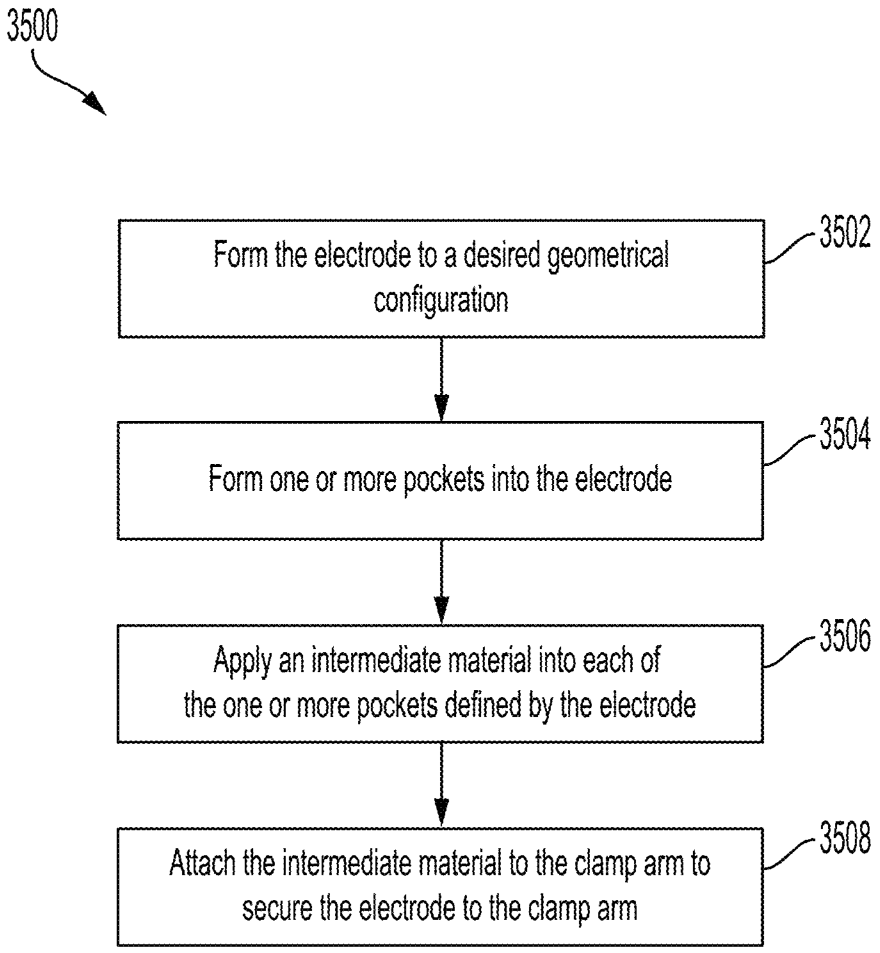
FIG. 14 illustrates a method of manufacturing the electrode of FIG. 13, in accordance with at least one non-limiting aspect of the present disclosure.

Referring now to FIG. 14, a method 3500 of manufacturing the electrode 3400 of FIG. 13 is depicted in accordance with at least one non-limiting aspect of the present disclosure. According to the non-limiting aspect of FIG. 13, the method 3500 can include forming 3502, the electrode 3400 (FIG. 13) until a desired geometrical configuration is achieved. Any conventional processes, including the processes disclosed herein can be used to machine the electrode 3400 (FIG. 13). The method 3500 can further include forming 3504 the one or more pockets 3410 (FIG. 13) into the electrode 3400 (FIG. 13). Each pocket should be dimensioned (e.g., 0.02 inches deep) and machined to achieve a desired geometrical configuration and thus, facilitate a desired attachment of the electrode 3400 to the clamp arm. The forming 3504 can be performed using a 0.010-0.020 inch diameter end mill, for example, such that each pocket 3410 (FIG. 13) continues to a desired datum. Then the electrode 3400 (FIG. 13) can be tumbled to remove sharp edges. Assuming a desired stamping thickness (e.g., 0.025-0.027 inches), the length of each pocket 3410 can be determined. For example, it may be desirable to define each pocket with a length of 0.06-0.07 inches.

According to the non-limiting aspect of FIG. 14, the method 3500 can further include applying 3506 an intermediate material, such as stainless steel, into each of the one or more pockets 3410 (FIG. 13) defined by the electrode 3400 (FIG. 13). For example, the applying 3506 can be performed via a thermal spray. The spray may continue until the intermediate material arrives at a datum or achieves a desired thickness (e.g., 0.020 inches thick, plus or minus 0.002 inches). According to some non-limiting aspects, each pocket can be filled in with a 17-4 material and bonded to aluminum. The method 3500 can further include attaching 3508 the intermediate material to the clamp arm to secure the electrode 3400 (FIG. 13) to the clamp arm. Any process, including laser welding, can be used for the attachment. The laser weld of the electrode 3400 (FIG. 13) to a stainless steel (e.g., 17-4) clamp arm can be done using, for example, a preferable spot (e.g., 0.015 inch diameter) and a preferable weld penetration depth (e.g., 0.002-0.004 inches). According to other non-limiting aspects, two spots can be overlapping onto each oval shape (e.g., a 50% overlap) to comply with particular welding requirements.

Of course, the steps of the method 3500 of FIG. 14 are non-exclusive and thus, the method 3500 can include additional steps in other non-limiting aspects. For example, the method 3500 can be modified to include any other manufacturing processes disclosed herein to achieve any features of any of the surgical devices, generators, end effectors, control circuits, sensors, and/or other components disclosed herein.

EXAMPLES

Examples of various aspects of end-effectors and surgical instruments of the present disclosure are provided below. An aspect of the end-effector or surgical instrument may include any one or more than one, and any combination of, the examples described below:

Example 1. A surgical device, including: an end effector including a clamp jaw configured to grasp tissue; a trigger configured to open and close the clamp jaw about the tissue; a sensor configured to detect a relative position of the trigger and generate a first signal associated with the detected relative position of the trigger; and a control circuit communicably coupled to the sensor and configured to communicate with a generator, wherein the control circuit is configured to: transmit a second signal to the generator to cause the generator to administer energy associated with a surgical operation to be performed on the tissue; receive the first signal from the sensor; determine that clamp jaws are not positioned to administer the energy associated with the surgical operation based, at least in part, on the first signal; and cause the generator to administer energy configured to release the tissue from a blade in response to determining that the clamp jaws are opened sufficiently wherein a parameter of the energy configured to release the tissue from the blade is different than a parameter of the energy associated with a surgical operation to be performed on the tissue.

Example 2. The surgical device of Example 1, wherein the energy configured to release the tissue from the blade is ultrasonic.

Example 3. The surgical device of any one of Examples 1-2, wherein the parameter of the energy configured to release the tissue from the blade includes at least one of a magnitude, a frequency, or an amplitude, or any combinations thereof.

Example 4. The surgical device of any one of Examples 1-3, wherein the parameter of the energy configured to release the tissue from the has a duration selected in a range of 0.1 to 1.0 seconds.

Example 5. The surgical device of any one of Examples 1-4, wherein the energy configured to release the tissue from the blade is administered at a percentage of a current set point.

Example 6. The surgical device of any one of Examples 1-5, wherein the percentage is selected in a range of 50% to 120% of maximum energy output.

Example 7. The surgical device of any one of Examples 1-6, wherein the control circuit is further configured to:

determine that a closure of the clamp jaws has initiated about the tissue based, at least in part, on the first signal; and prevent the generator from administering the energy configured to release the tissue from the blade in response to determining that the closure of the clamp jaws has initiated.

Example 8. The surgical device of any one of Examples 1-7, wherein the control circuit is further configured to: determine that a closure of the clamp jaws has initiated about the tissue based, at least in part, on the first signal; and adjust the parameter of the of energy configured to release the tissue from the blade until it is the same as the parameter of the energy associated with a surgical operation to be performed on the tissue.

Example 9. An end effector configured for use with a surgical device, the end effector including: a clamp arm base; a clamp arm pad including a first geometry; an ultrasonic blade including a first hardness; and a second electrode including: an electrode material including a second hardness, wherein the second hardness is less than the first hardness of the ultrasonic blade, and wherein the electrode material defines a cavity including a second geometry, wherein the second geometry corresponds to the first geometry such that a portion of the clamp arm pad can be positioned within the cavity; and an intermediate material configured to join the electrode material to the clamp arm base.

Example 10. The end effector of Example 9, wherein the intermediate material is welded to the clamp arm base.

Example 11. The end effector of any one of Examples 9-10, wherein the electrode material is cladded to the intermediate material.

Example 12. The end effector of any one of Examples 9-11, wherein the electrode material further defines a pocket configured to accommodate the intermediate material, and wherein the intermediate material is positioned within the pocket.

Example 13. The end effector of any one of Examples 9-12, wherein the electrode material is at least one of an aluminum-based material, a copper-based material, or a titanium-based material, and wherein the intermediate material is a stainless steel.

Example 14. The end effector of any one of Examples 9-13, wherein the clamp arm pad is constructed from a non-stick, PTFE material.

Example 15. The end effector of any of Examples 9-14, wherein the clamp arm pad includes a first thickness that corresponds to a rated life of the clamp arm pad.

Example 16. The end effector of any of Examples 9-15, wherein the electrode material includes a second thickness, and wherein the intermediate material includes a third thickness that is less than the second thickness.

Example 17. The end effector of any one of Examples 9-16, wherein the electrode material includes a second thickness, and wherein the intermediate material includes a third thickness that is greater than the second thickness.

Example 18. A method of manufacturing an electrode configured for use within an end effector of a surgical device, the method including: forming an electrode material into a desired geometrical configuration; forming one or more pockets into the electrode material; applying an intermediate material into the one or more pockets formed into the electrode, wherein the intermediate material is suited for welding; bonding the intermediate material to the electrode material; and attaching the intermediate material to a clamp arm base of the end effector to secure the intermediate material and electrode material to the clamp arm base.

Example 19. The method of Examples 18, wherein applying the intermediate material includes spraying the intermediate material into the one or more pockets.

Example 20. The method of any either of Examples 18-19, wherein spraying the intermediate material into the one or more pockets includes thermal spraying the intermediate material into the one or more pockets.

Example 21. The method of any one of Examples 18-20, wherein attaching the intermediate material to the clamp arm base includes at least one of welding, brazing, adhering, or soldering the intermediate material to the clamp arm base.

Example 22. The method of any one of Examples 18-21, wherein attaching the intermediate material to the clamp arm base includes laser welding the intermediate material to the clamp arm base.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. An end effector configured for use with a surgical device, the end effector comprising:
- a clamp arm, comprising:
  - a clamp arm base;
  - a clamp arm pad comprising a first geometry;
  - an electrode comprising an electrode material; and
  - an intermediate material configured to join the electrode material to the clamp arm base; and
- an ultrasonic blade having a first hardness,
  - wherein the electrode material has a second hardness, wherein the second hardness is less than the first hardness of the ultrasonic blade, and wherein the electrode material defines a cavity comprising a second geometry, wherein the second geometry corresponds to the first geometry such that a portion of the clamp arm pad can be positioned within the cavity.

2. The end effector of claim 1, wherein the intermediate material is welded to the clamp arm base.

3. The end effector of claim 1, wherein the electrode material is cladded to the intermediate material.

4. The end effector of claim 1, wherein the electrode material further defines a pocket configured to accommodate the intermediate material, and wherein the intermediate material is positioned within the pocket.

5. The end effector of claim 1, wherein the electrode material is at least one of an aluminum-based material, a copper-based material, or a titanium-based material, and wherein the intermediate material is a stainless steel.

6. The end effector of claim 1, wherein the clamp arm pad is constructed from a non-stick, PTFE material.

7. The end effector of claim 1, wherein the clamp arm pad has a first thickness that corresponds to a rated life of the clamp arm pad.

8. The end effector of claim 7, wherein the electrode material has a second thickness, and wherein the intermediate material has a third thickness that is less than the second thickness.

9. The end effector of claim 7, wherein the electrode material has a second thickness, and wherein the intermediate material has a third thickness that is greater than the second thickness.

* * * * *